(12) United States Patent
Tsubuku et al.

(10) Patent No.: US 9,681,912 B2
(45) Date of Patent: Jun. 20, 2017

(54) GRASPING TREATMENT APPARATUS

(71) Applicant: OLYMPUS CORPORATION, Hachioji-shi, Tokyo (JP)

(72) Inventors: Yoshihiro Tsubuku, Fuchu (JP); Minoru Kawasaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/175,837

(22) Filed: Jun. 7, 2016

(65) Prior Publication Data

US 2016/0287317 A1 Oct. 6, 2016

Related U.S. Application Data

(63) Continuation of application No. PCT/JP2015/052866, filed on Feb. 2, 2015.

(30) Foreign Application Priority Data

Feb. 17, 2014 (JP) ................ 2014-027987

(51) Int. Cl.
*A61B 18/14* (2006.01)
*A61B 17/32* (2006.01)
*A61B 18/00* (2006.01)

(52) U.S. Cl.
CPC .. *A61B 18/1445* (2013.01); *A61B 17/320092* (2013.01); *A61B 2018/0019* (2013.01);
(Continued)

(58) Field of Classification Search
CPC ............ A61B 18/1442; A61B 18/1445; A61B 2018/1452; A61B 2018/00994;
(Continued)

(56) References Cited

U.S. PATENT DOCUMENTS 9,226,767 B2 * 1/2016 Stulen ............... A61B 17/32009
2009/0259221 A1 10/2009 Tahara et al.
(Continued)

FOREIGN PATENT DOCUMENTS

| JP | 2009-254818 A | 11/2009 |
|----|---------------|---------|
| JP | 2010-005370 A | 1/2010 |
| WO | 2010/076869 A1 | 7/2010 |

OTHER PUBLICATIONS

Apr. 21, 2015 Search Report issued in International Patent Application No. PCT/JP2015/052866.

*Primary Examiner* — Thomas Giuliani
(74) *Attorney, Agent, or Firm* — Oliff PLC

(57) ABSTRACT

A grasping treatment apparatus includes an ultrasonic control section stopping an output of a vibration generating electric power or outputting the vibration generating electric power in a second ultrasonic output mode where incision performance provided by an ultrasonic vibration in a treatment section becomes smaller than that in a first ultrasonic output mode before a peak detection point. The grasping treatment apparatus includes a high-frequency control section outputting a high-frequency electric power in a second high-frequency output mode where incision performance provided by a high-frequency current flowing between a probe electrode portion and a jaw electrode portion becomes higher than that in a first high-frequency output mode before the peak detection point.

11 Claims, 14 Drawing Sheets

(52) U.S. Cl.
CPC ............... *A61B 2018/0072* (2013.01); *A61B 2018/00589* (2013.01); *A61B 2018/00601* (2013.01); *A61B 2018/00607* (2013.01); *A61B 2018/00642* (2013.01); *A61B 2018/00666* (2013.01); *A61B 2018/00708* (2013.01); *A61B 2018/00714* (2013.01); *A61B 2018/00767* (2013.01); *A61B 2018/00875* (2013.01); *A61B 2018/00994* (2013.01); *A61B 2018/1452* (2013.01)

(58) Field of Classification Search
CPC .. A61B 2018/00875; A61B 2018/0019; A61B 2018/00607; A61B 17/320092
USPC ................. 606/41, 50–52, 169, 205, 207
See application file for complete search history.

(56) References Cited

U.S. PATENT DOCUMENTS

| | | | |
|---|---|---|---|
| 2009/0326569 A1 | 12/2009 | Tanaka et al. | |
| 2010/0168742 A1 | 7/2010 | Shibata | |
| 2012/0310264 A1* | 12/2012 | Messerly | A61B 17/32009 606/169 |
| 2013/0282038 A1 | 10/2013 | Dannaher et al. | |
| 2015/0164538 A1* | 6/2015 | Aldridge | A61B 17/32009 606/52 |
| 2016/0256190 A1* | 9/2016 | Tsubuku | A61B 17/32009 |

* cited by examiner

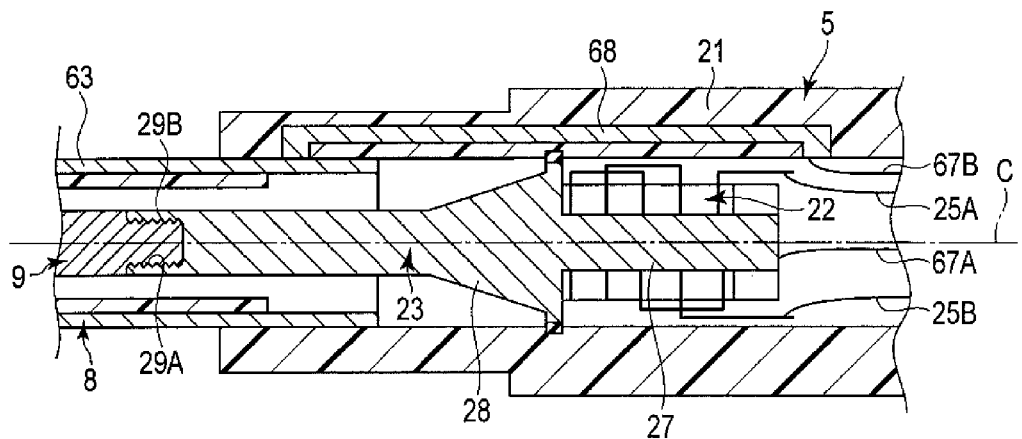
F I G. 2
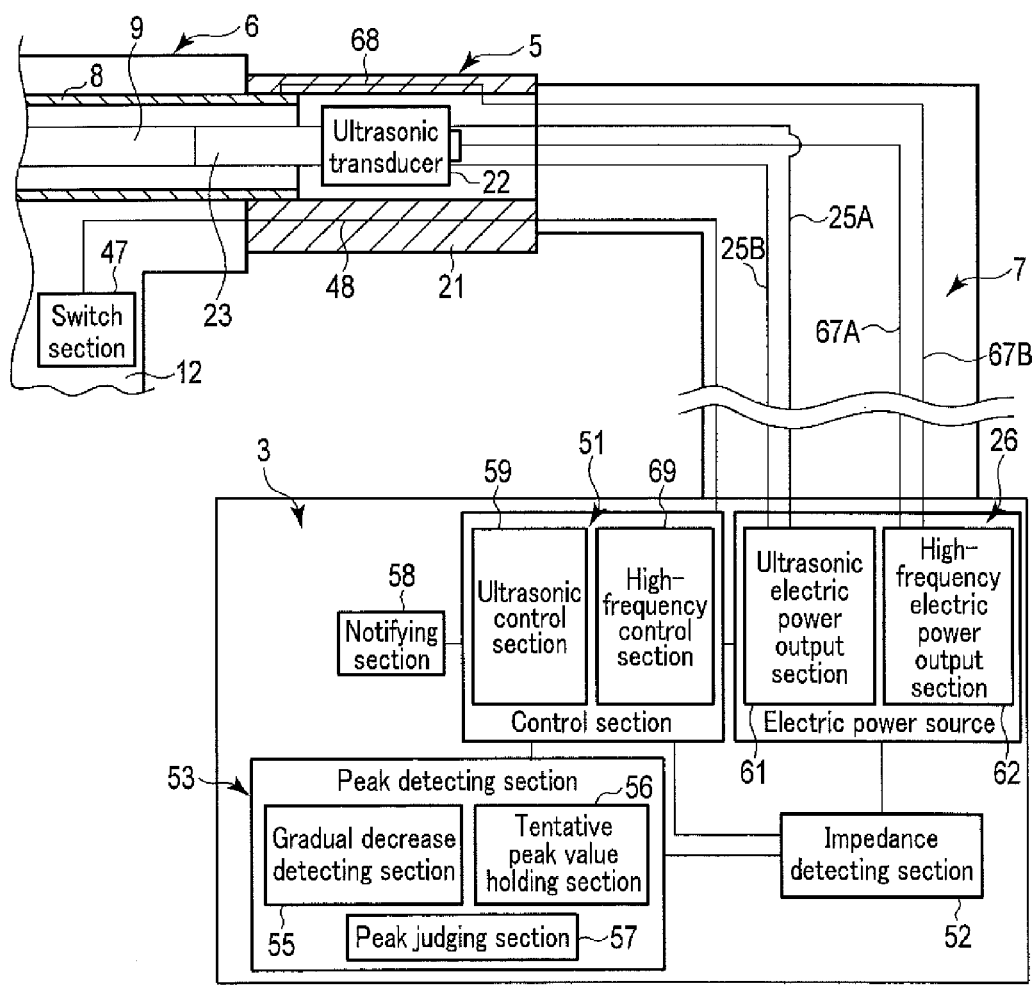
F I G. 3

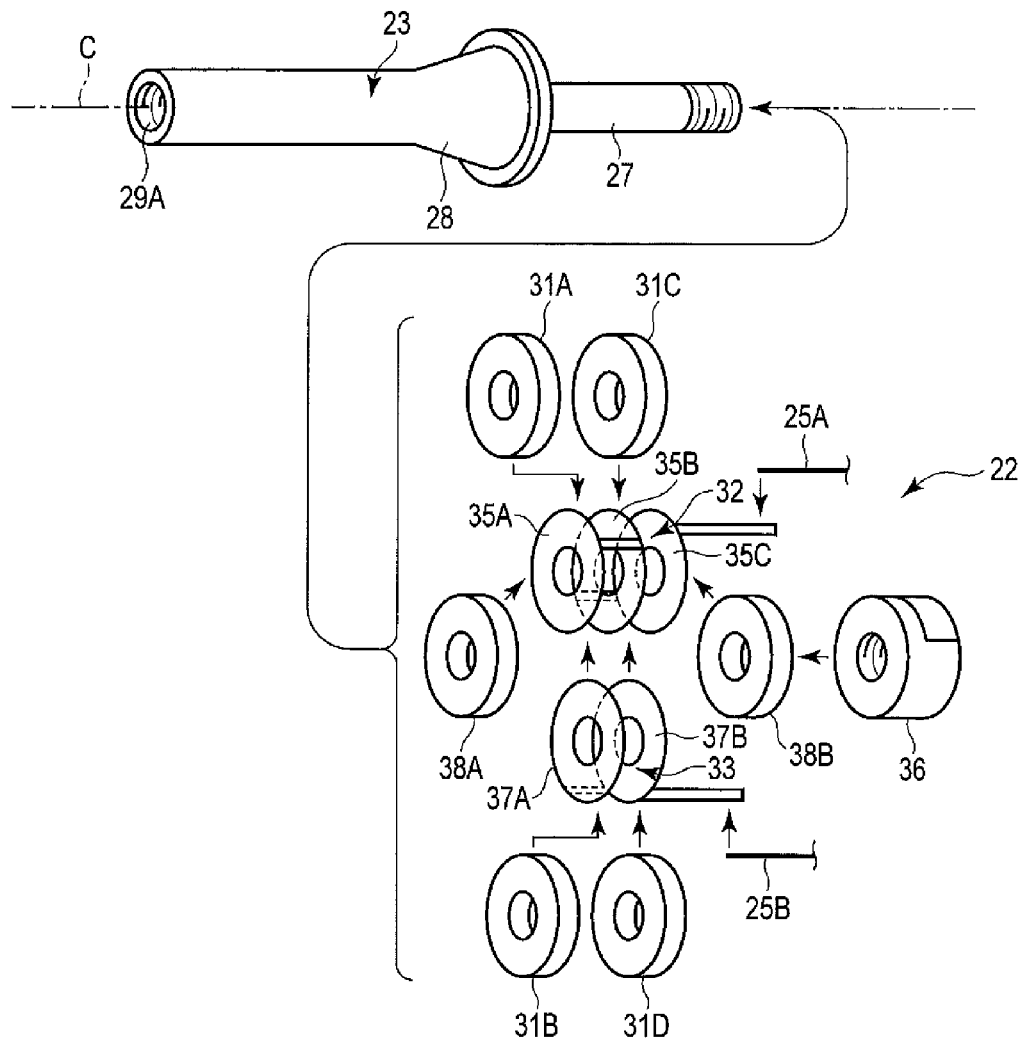
F I G. 4
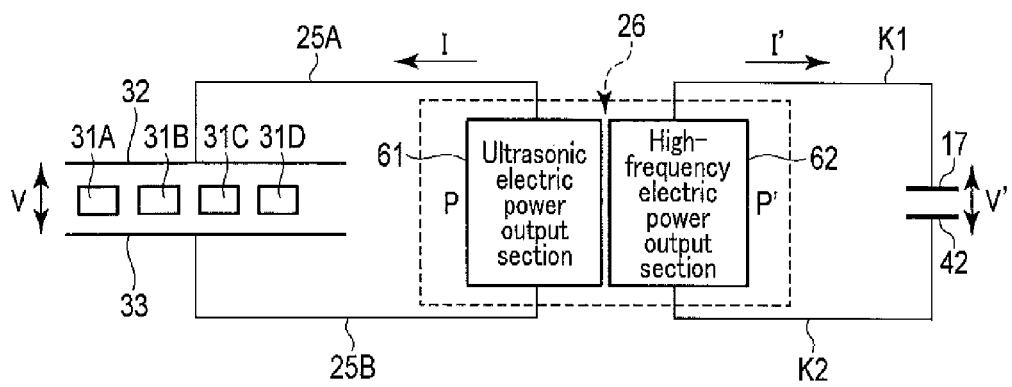
F I G. 5

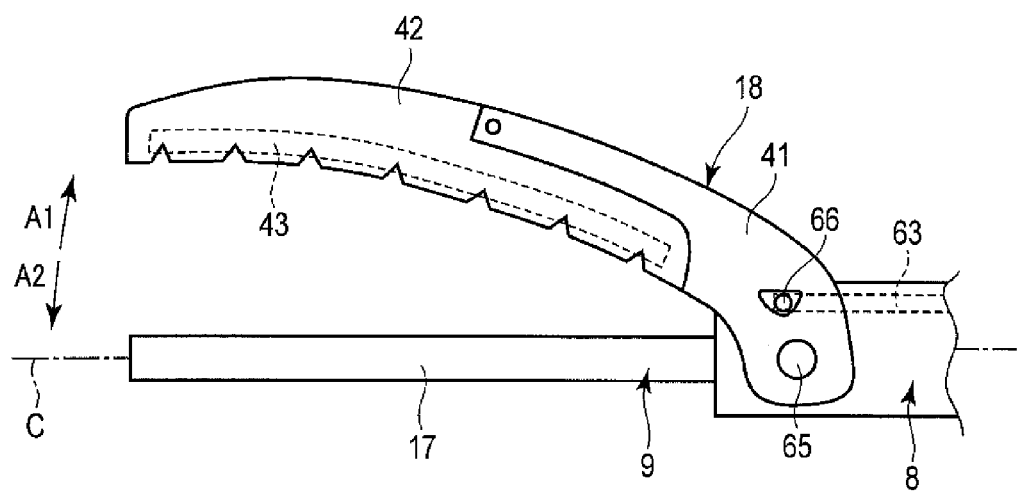
F I G. 6
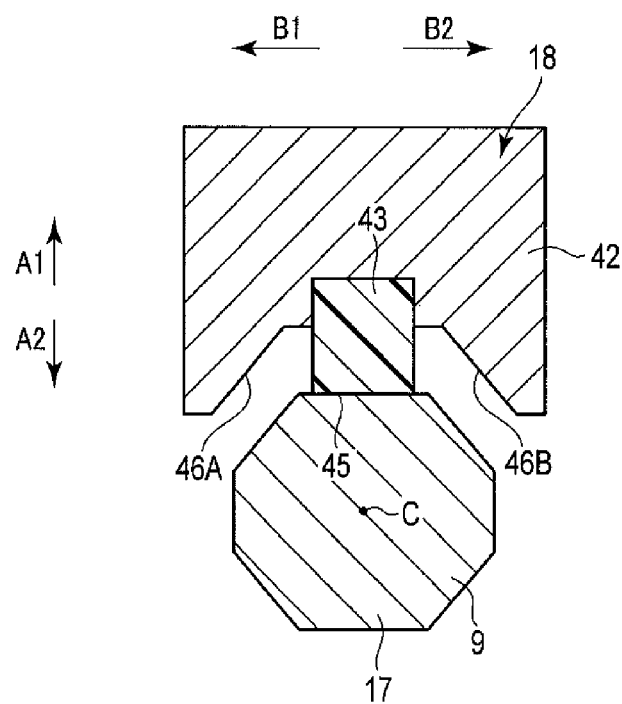
F I G. 7

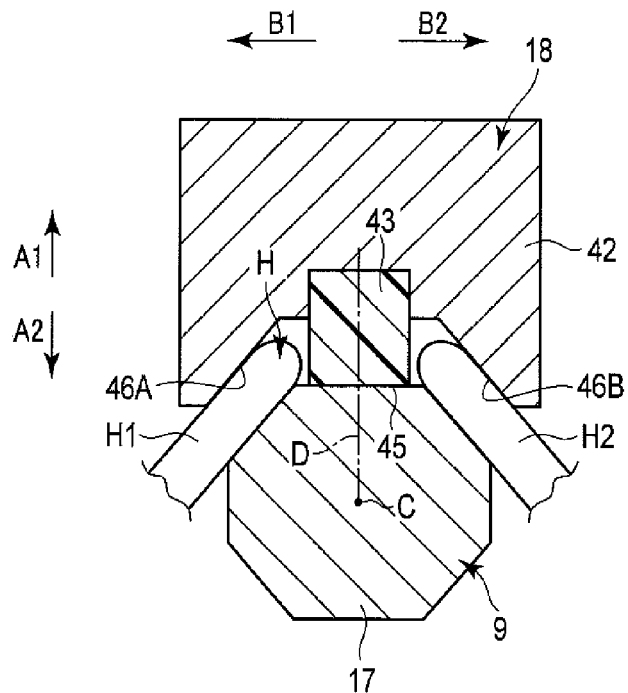
F I G. 8
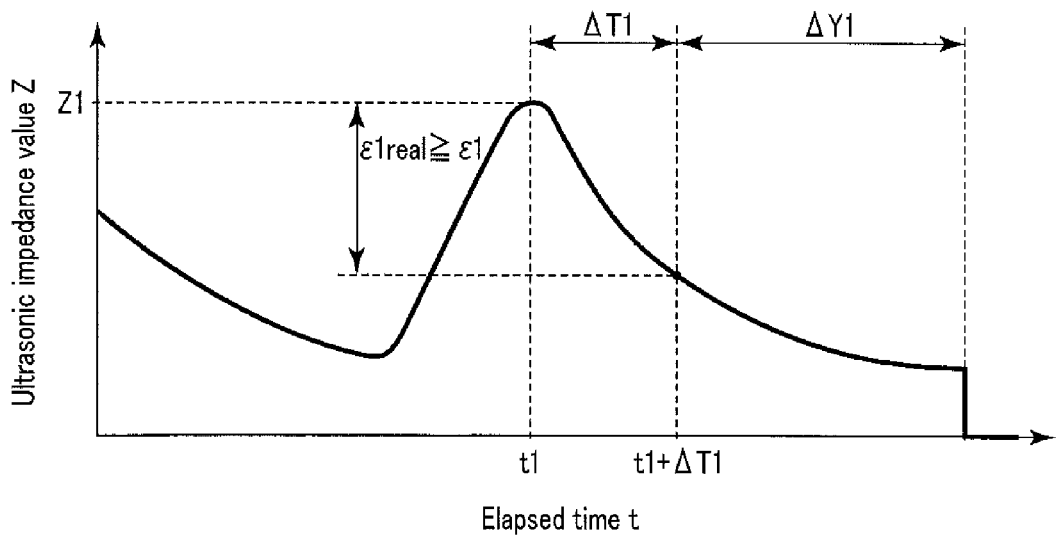
F I G. 9

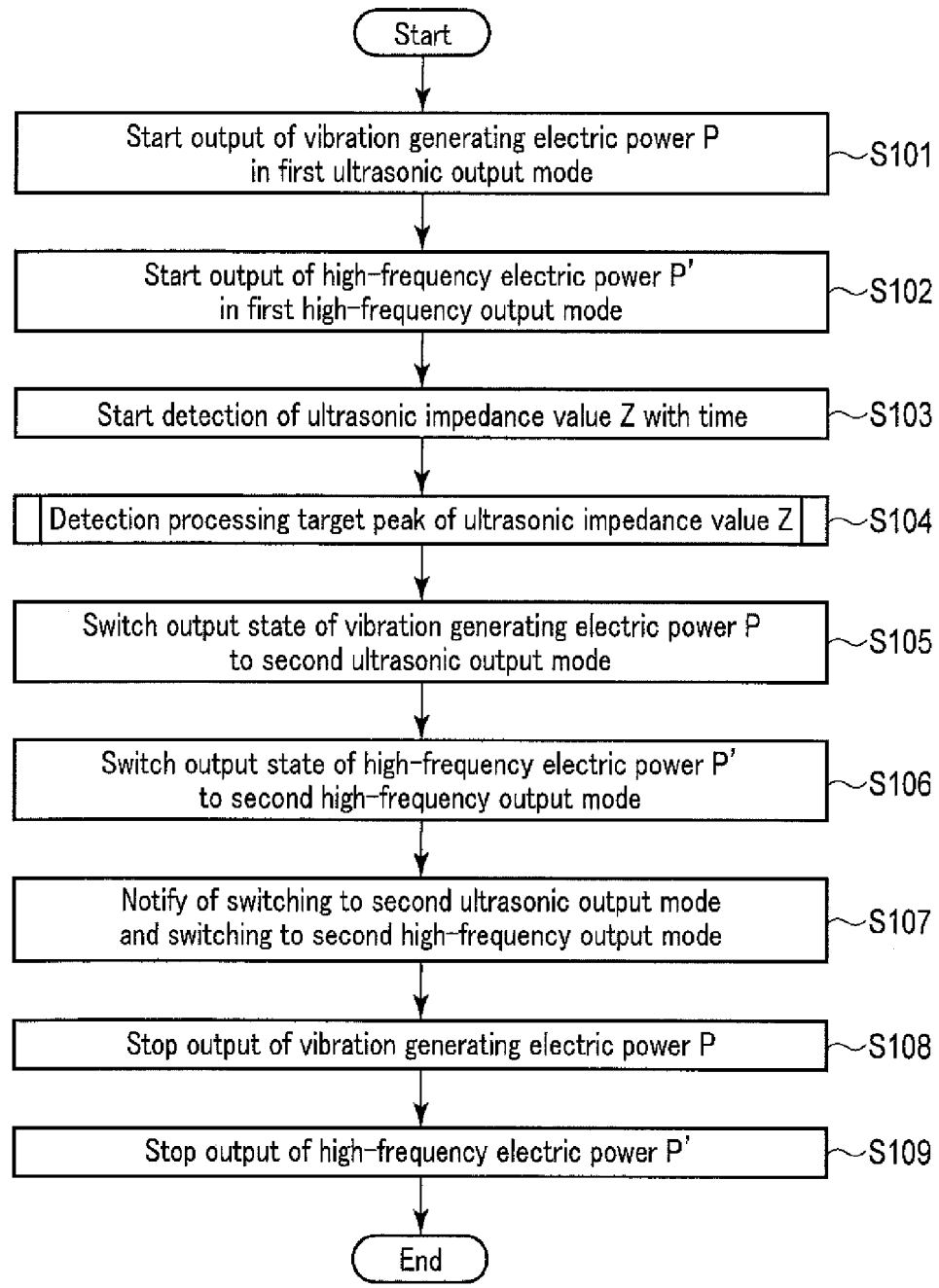
F I G. 10

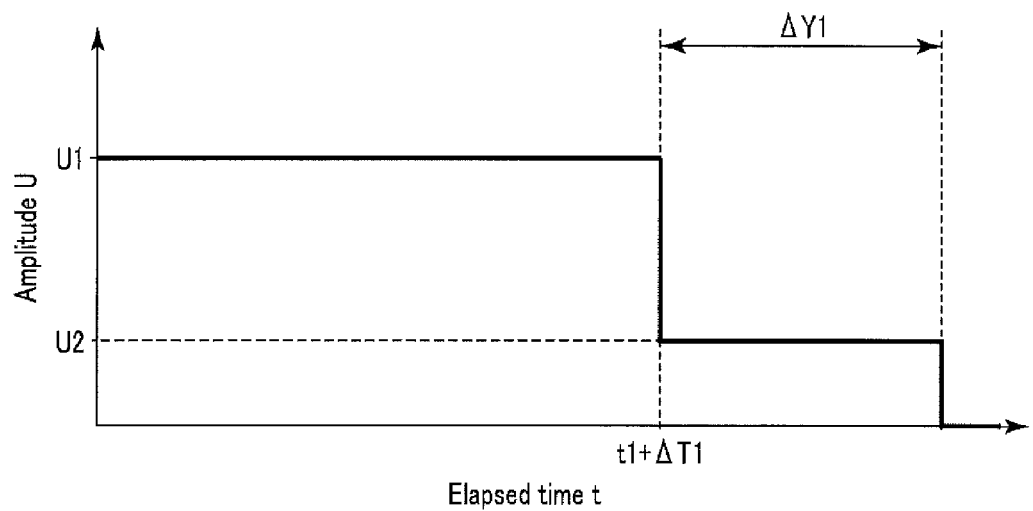
F I G. 11

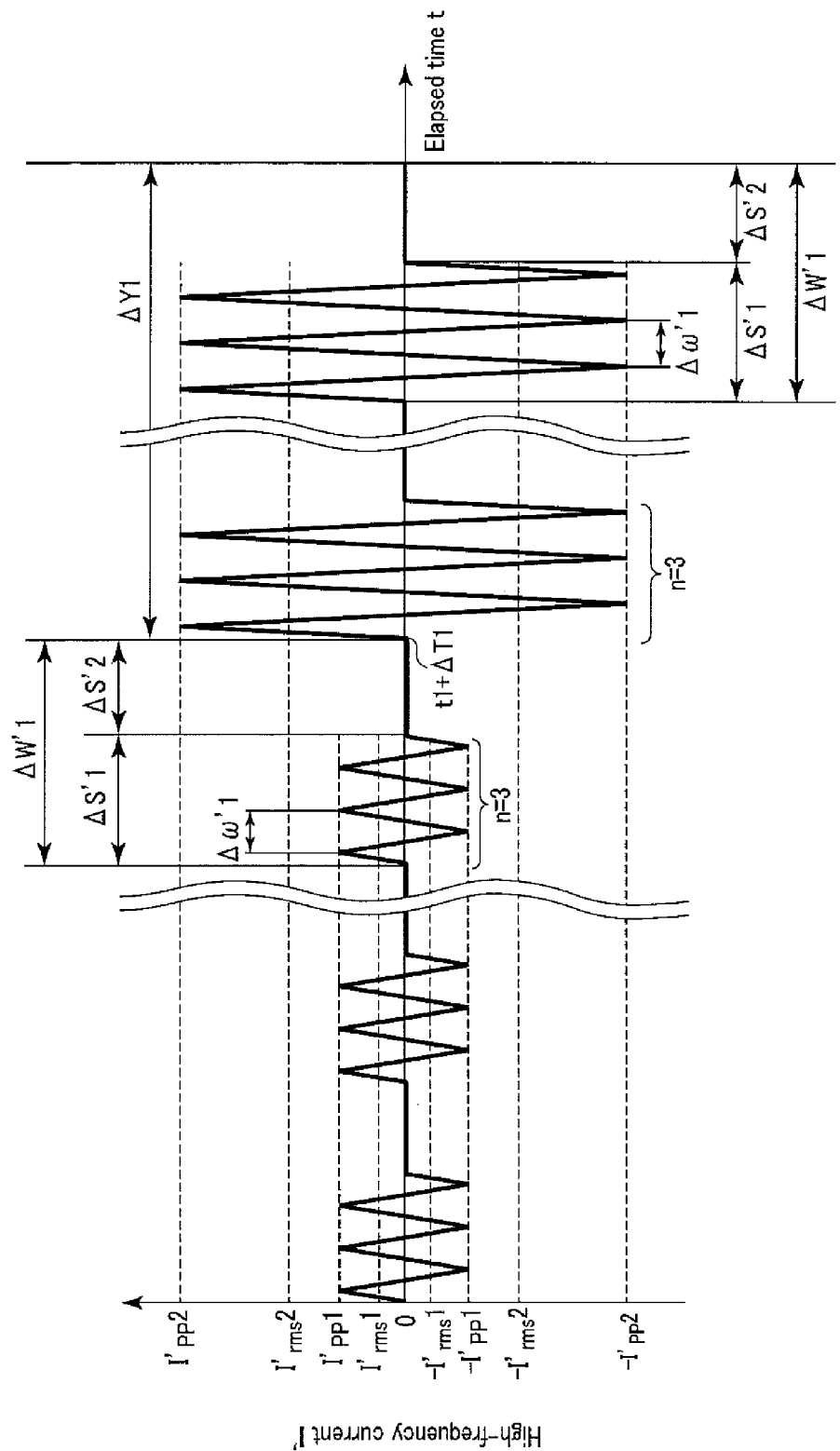
F I G. 12

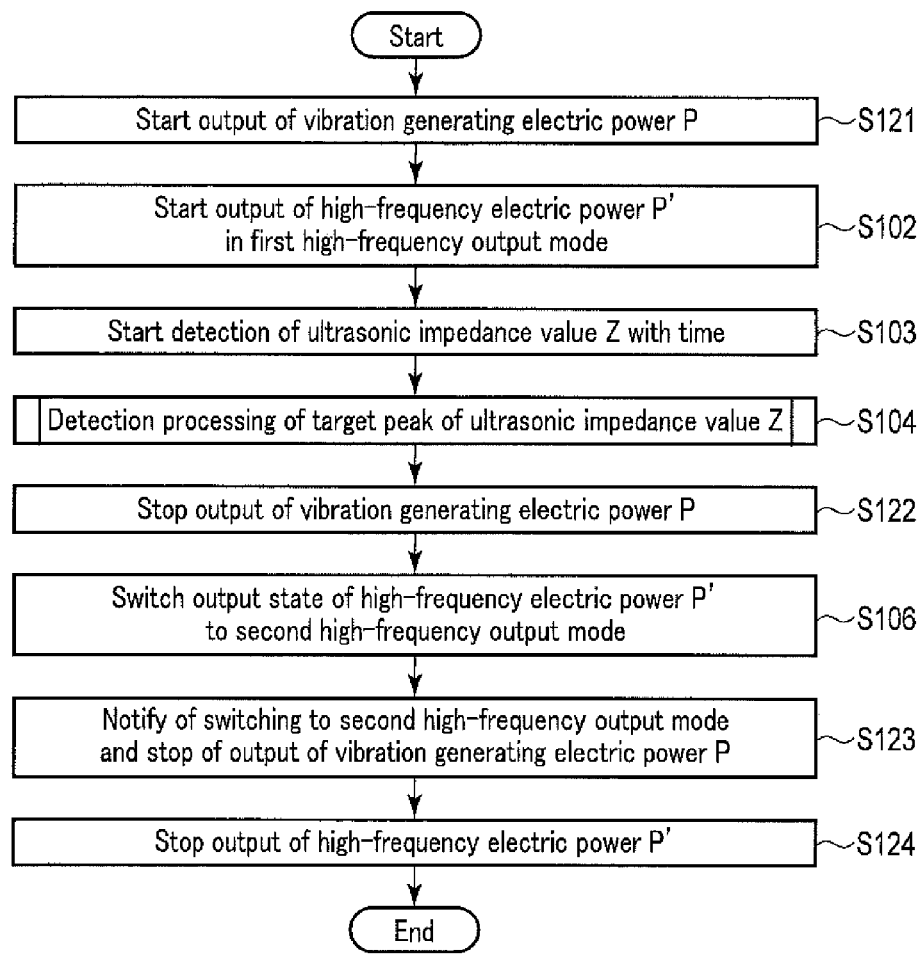
F I G. 15
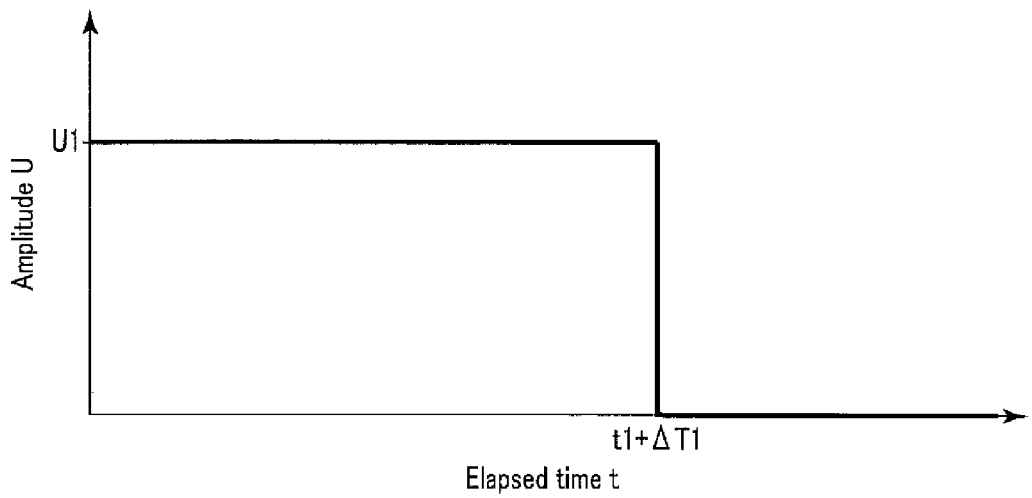
F I G. 16

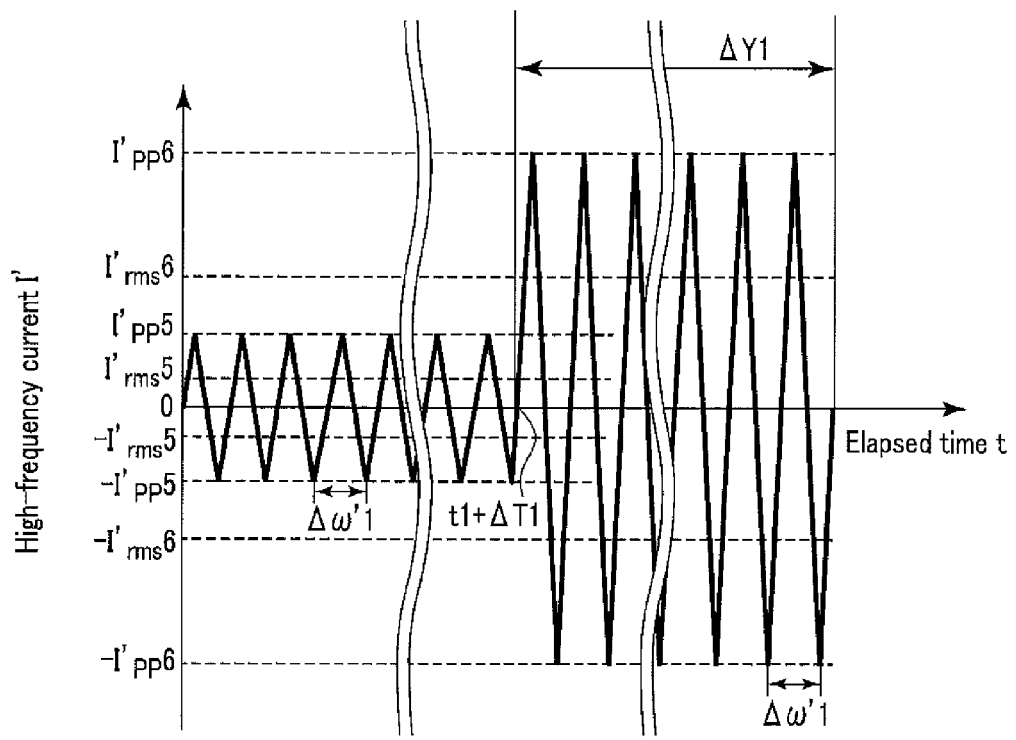
F I G. 20

GRASPING TREATMENT APPARATUS

CROSS-REFERENCE TO RELATED APPLICATIONS

This is a Continuation application of PCT Application No. PCT/JP2015/052866, filed Feb. 2, 2015 and based upon and claiming the benefit of priority from prior Japanese Patent Application No. 2014-027987, filed Feb. 17, 2014, the entire contents of which are incorporated herein by reference.

BACKGROUND OF THE INVENTION

1. Field of the Invention

The present invention relates to a grasping treatment apparatus which grasps a treated target between a treatment section to which an ultrasonic vibration is transmitted and a jaw which is openable and closable relative to the treatment section, allows a high-frequency electric power to be supplied to the treatment section and the jaw, and gives a treatment to the grasped treated target by using the ultrasonic vibration and the high-frequency current.

2. Description of the Related Art

For example, U.S. Patent Application Publication No. 2012/0310264 discloses a grasping treatment apparatus (ultrasonic treatment apparatus) which includes a treatment section to which an ultrasonic vibration is transmitted and a jaw openable and closable relative to the treatment section. In this grasping treatment apparatus, when vibration generating electric power is transmitted from an electric power source to a vibration generating section, the ultrasonic vibration is generated in an ultrasonic transducer which is the vibration generating section. Then, the generated ultrasonic vibration is transmitted to the treatment section, and the treatment section treats a treated target such as a biological tissue by use of the transmitted ultrasonic vibration. Here, opening and closing directions of the jaw are perpendicular (transverse) to a transmitting direction of the ultrasonic vibration. When the ultrasonic vibration is transmitted to the treatment section in a state where the treated target is grasped between the treatment section and the jaw, frictional heat is generated between the treated target and the treatment section. By the frictional heat, the treated target is coagulated and simultaneously incised. Furthermore, in the ultrasonic treatment apparatus, an ultrasonic impedance value of the vibration generating electric power is detected with time, and it is judged whether the ultrasonic impedance value is within a range of a first default threshold or more and a second default threshold or less, the second threshold being greater than the first threshold.

Further, in the grasping treatment apparatus of U.S. Patent Application Publication No. 2012/0310264, a high-frequency electric power is output from an electric power source. When the high-frequency electric power is supplied to the treatment section, the treatment section functions as a probe electrode portion. Furthermore, the high-frequency electric power is supplied to a jaw electrode portion of the jaw. The treated target griped between the treatment section and the jaw is subjected to a bipolar treatment by using the treatment section and the jaw electrode portion as electrodes. In the bipolar treatment, the high-frequency current flows between the treatment section (the probe electrode portion) and the jaw electrode portion through the treated target. The high-frequency current denatures and coagulates the treated target.

BRIEF SUMMARY OF THE INVENTION

According to one aspect of the invention, a grasping treatment apparatus includes that: an electric power source configured to output a vibration generating electric power and a high-frequency electric power; a vibration generating section configured to generate an ultrasonic vibration when the vibration generating electric power is supplied from the electric power source; a treatment section to which the ultrasonic vibration generated in the vibration generating section and the high-frequency electric power generated in the electric power source are transmitted, and which is configured to perform a treatment by use of the transmitted ultrasonic vibration and high-frequency electric power, the treatment section including a probe electrode portion configured to function as an electrode when the high-frequency electric power is supplied thereto; a jaw which is openable and closable relative to the treatment section, the jaw including an abutment portion abutable with the treatment section in a state where the jaw is closed relative to the treatment section, and a jaw electrode portion configured to function as an electrode different from the probe electrode portion when the high-frequency electric power is supplied thereto; an impedance detecting section configured to detect an ultrasonic impedance value of the vibration generating electric power with time, in a state where the vibration generating electric power is output from the electric power source; a gradual decrease detecting section configured to detect a gradual decrease start point to start gradual decrease of the ultrasonic impedance value on the basis of detection results in the impedance detecting section; a tentative peak value holding section configured to hold the ultrasonic impedance value at the detected gradual decrease start point as a tentative peak value; a peak judging section configured to judge whether or not the held tentative peak value is a target peak of a detection target by comparing, to the held tentative peak value, changes with time of the ultrasonic impedance value after the gradual decrease start point; an ultrasonic control section configured to control an output state of the vibration generating electric power from the electric power source, the ultrasonic control section being configured to stop an output of the vibration generating electric power from the electric power source or configured to output the vibration generating electric power from the electric power source in a second ultrasonic output mode where incision performance provided by the ultrasonic vibration in the treatment section becomes smaller than that in a first ultrasonic output mode before a judgment point at which the tentative peak value is determined to be the target peak, on the basis of the fact that the tentative peak value is determined to be the target peak value by the peak judging section; and a high-frequency control section configured to control an output state of the high-frequency electric power from the electric power source, the high-frequency control section being configured to output the high-frequency electric power from the electric power source in a second high-frequency output mode where incision performance provided by a high-frequency current flowing between the probe electrode portion and the jaw electrode portion becomes higher than that in a first high-frequency output mode before the judgment point, on the basis of the fact that the tentative peak value is determined to be the target peak by the peak judging section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a longitudinal cross-sectional view schematically showing a configuration of a transducer unit, a proximal portion of a sheath, and a proximal portion of an ultrasonic probe according to the first embodiment;

FIG. 3 is a schematic view showing an electrical connection state in the transducer unit and a control unit according to the first embodiment;

FIG. 4 is a schematic view schematically showing each member of a horn member and an ultrasonic transducer in an exploded manner according to the first embodiment;

FIG. 5 is a schematic view showing an electrical path through which a vibration generating electric power and a high-frequency electric power output from an electric power source are supplied according to the first embodiment;

FIG. 6 is a side elevation schematically showing a treatment section and a jaw according to the first embodiment;

FIG. 7 is a transverse cross-sectional view schematically showing cross sections of the treatment section and the jaw perpendicular to a longitudinal axis according to the first embodiment;

FIG. 8 is a schematic view explaining cut-and-divided of a treated target grasped between the treatment section and the jaw according to the first embodiment;

FIG. 9 is a schematic view showing an example of changes with time of an ultrasonic impedance value from start of an output of the vibration generating electric power from the electric power source according to the first embodiment;

FIG. 10 is a flowchart showing an actuating state of the control unit from start of the output of the vibration generating electric power and an output of the high-frequency electric power according to the first embodiment;

FIG. 11 is a schematic view showing an example of changes with time of an amplitude of the ultrasonic vibration in the treatment section according to the first embodiment;

FIG. 12 is a schematic view showing an example of changes with time of a high-frequency current flowing between the treatment section and the grasping member according to the first embodiment;

FIG. 15 is a flowchart showing an actuating state from start of an output of the vibration generating electric power and an output of the high-frequency electric power of the control unit according to a second modification;

FIG. 16 is a schematic view showing an example of changes with time of the amplitude of the ultrasonic vibration in the treatment section according to the second modification;

FIG. 20 is a schematic view showing an example of changes with time of the high-frequency current flowing between the treatment section and the grasping member according to a six modification.

DETAILED DESCRIPTION OF THE INVENTION (First Embodiment)

Figure 1:
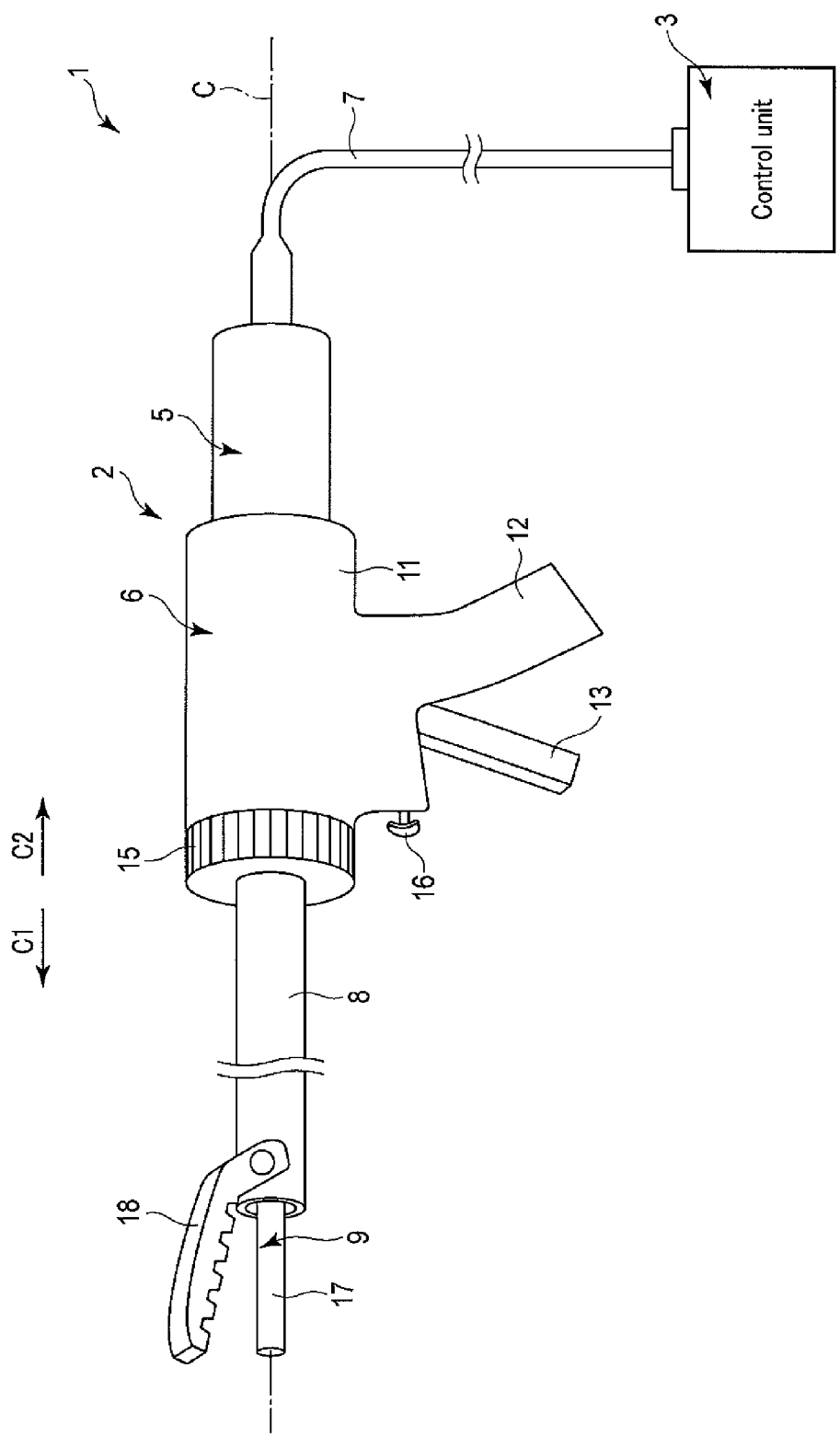
FIG. 1 is a schematic view showing a grasping treatment apparatus according to a first embodiment.

A first embodiment according to the present invention will now be described with reference to FIG. 1 to FIG. 13. FIG. 1 is a view showing a grasping treatment apparatus 1. As shown in FIG. 1, the grasping treatment system (surgical treatment apparatus) 1 includes a grasping treatment instrument (a hand piece) 2, and a control unit 3. The grasping treatment tool 2 used as an ultrasonic treatment tool and a high-frequency treatment tool has a longitudinal axis C. One of two directions parallel to the longitudinal axis C is a distal direction (a direction of an arrow C1 in FIG. 1), and an opposite direction of the distal direction is a proximal direction (a direction of an arrow C2 in FIG. 1). The grasping treatment instrument 2 includes a transducer unit 5 and a handle unit 6. The vibrator unit 5 is detachably coupled with a proximal direction side of the handle unit 6. One end of a cable 7 is connected to a proximal portion of the transducer unit 5. The other end of the cable 7 is connected to the control unit 3.

The handle unit 6 includes a tubular case portion 11 extended along the longitudinal axis C, a fixed handle 12 integrally formed with the tubular case portion 11, and a movable handle 13 coupled to the tubular case portion 11 to allow its turning motion. The fixed handle 12 is extended in a state that it is apart from the tubular case portion 11 to the longitudinal axis C. When the movable handle 13 turns around a position at which it is attached to the tubular case portion 11, the movable handle 13 opens or closes relative to the fixed handle 12. Further, the handle unit 6 includes a rotary operation knob 15 attached on a distal direction side of the tubular case portion 11. The rotary operation knob 15 can rotate around the longitudinal axis C relative to the tubular case portion 11. Furthermore, an energy operation input button 16 which is an energy operation input section is provided to the fixed handle 12.

The grasping treatment instrument 2 includes a sheath 8 extended along the longitudinal axis C. The sheath 8 is inserted into the rotary operation knob 15 and into the tubular case portion 11 from the distal direction side, and the sheath 8 is attached to the handle unit 6. Moreover, the grasping treatment instrument 2 includes an ultrasonic probe 9. The ultrasonic probe 9 is extended along the longitudinal axis C from an inside of the tubular case portion 11 through an inside of the sheath 8. The ultrasonic probe 9 is inserted through the sheath 8. Additionally, a treatment section 17 protruding from a distal end of the sheath 8 toward the distal direction is provided in a distal portion of the ultrasonic probe 9.

A jaw 18 is attached to the distal portion of the sheath 8 to allow its turning motion. The sheath 8, the ultrasonic probe 9, and the jaw 18 can rotate together with the rotary operation knob 15 around the longitudinal axis C relative to the tubular case portion 11. Further, the transducer unit 5 includes a transducer case 21. When the vibrator case 21 is inserted into the tubular case portion 11 from the proximal direction side, the transducer unit 5 is coupled to the handle unit 6. Inside the tubular case portion 11, the vibrator case 21 is coupled with the sheath 8. The oscillator case 21 can rotate together with the rotary operation knob 15 around the longitudinal axis C relative to the tubular case portion 11.

FIG. 2 is a view showing configurations of the transducer unit 5, a proximal portion of the sheath 8, and a proximal portion of the ultrasonic probe 9. As shown in FIG. 2, the transducer unit 5 includes the transducer case 21, an ultrasonic transducer 22 which is a vibration generating section provided in the vibrator case 21, and a horn member 23 to which the ultrasonic vibrator 22 is attached. FIG. 3 is a view showing an electrical connection state of the transducer unit 5 and the control unit 3. As shown in FIG. 2 and FIG. 3, one end of each of electrical wiring portions 25A and 25B is connected to the ultrasonic transducer 22. The control unit 3 includes an electric power source 26 configured to output a vibration generating electric power P and a high-frequency electric power P'. The electric power source 26 includes an ultrasonic electric power output section 61 configured to output the vibration generating electric power P and a high-frequency electric power output section 62 configured to output the high-frequency electric power P'. In the ultrasonic electric power output section 61, for example, an electric power from, e.g., a receptacle outlet is converted into the vibration generating electric power P by a conversion circuit or the like, and the vibration generating electric power P is output. Further, in the high-frequency electric power output section 62, for example, the electric power from, e.g., a receptacle outlet is converted into the high-frequency electric power P' by a conversion circuit or the like, and the high-frequency electric power P' is output. The ultrasonic electric power output section 61 and the high-frequency electric power output section 62 may be integrally formed or may be separately formed. The other end of each of the electrical wiring portions 25A and 25B is connected to the ultrasonic electric power output section 61 of the electric power source 26. The vibration generating electric power P output from the ultrasonic electric power output section 61 is supplied to the ultrasonic vibrator 22 through the electrical wiring portions 25A and 25B. When the vibration generating electric power P is supplied, an ultrasonic vibration is produced in the ultrasonic transducer 22.

A transducer mounting portion 27 to which the ultrasonic transducer 22 is mounted is provided to the horn member 23. The ultrasonic vibration produced by the ultrasonic vibrator 22 is transmitted to the horn member 23. Furthermore, a sectional area change portion 28 is provided to the horn member 23 on the distal direction side with respect to the transducer mounting portion 27. In the sectional area change portion 28, a sectional area perpendicular to the longitudinal axis C decreases toward the distal direction. The sectional area change portion 28 enlarges an amplitude of the ultrasonic vibration. A female screw portion 29A is provided in a distal portion of the horn member 23. Moreover, a male screw portion 29B is provided in a proximal portion of the ultrasonic probe 9. When the male screw portion 29B is screwed into the female screw portion 29A, the ultrasonic probe 9 is connected to the distal direction side of the horn member 23. The ultrasonic probe 9 is connected to the horn member 23 inside the tubular case portion 11.

The ultrasonic vibration transmitted to the horn member 23 is transmitted from the proximal direction toward the distal direction along the longitudinal axis C in the horn member 23 and the ultrasonic probe 9. That is, the horn member 23 and the ultrasonic probe 9 are a vibration transmitting portion configured to transmit the generated ultrasonic vibration. The ultrasonic vibration is transmitted toward the distal direction until it reaches the treatment section 17. The treatment section 17 gives a treatment to, e.g., a biological tissue by using the transmitted ultrasonic vibration. It is to be noted that, in the vibration transmitting portion (the horn member 23 and the ultrasonic probe 9), the proximal end (the proximal end of the horn member 23) and the distal end (the distal end of the ultrasonic probe 9) are antinode positions of the ultrasonic vibration. Additionally, the ultrasonic vibration is longitudinal vibration whose vibrating direction and whose transmitting direction are parallel to the longitudinal axis C (the longitudinal axial direction). Thus, the distal direction parallel to the longitudinal axis C is the transmitting direction of the ultrasonic vibration. When the vibration transmitting portion transmits the ultrasonic vibration, the vibration transmitting portion including the treatment section 17 vibrates at a given resonance frequency F.

FIG. 4 is an exploded view showing each member in the horn member 23 and the ultrasonic transducer 22. As shown in FIG. 4, the ultrasonic vibrator 22 includes (four in this embodiment) ring-like piezoelectric elements 31A to 31D. The vibrator mounting portion 27 of the horn member 23 is inserted through the respective piezoelectric elements 31A to 31D. Further, the respective piezoelectric elements 31A to 31D are disposed on the transducer mounting portion 27 in a state that each of their thickness direction is parallel to the transmitting direction of the ultrasonic vibration (i.e., the longitudinal axis C) and each of their radial direction is perpendicular to the transmitting direction of the ultrasonic vibration (i.e., the distal end direction).

The ultrasonic oscillator 22 includes a first electrode portion 32 and a second electrode portion 33. One end of the electrical wiring portion 25A is connected to the first electrode portion 32, and one end of the electrical wiring portion 25B is connected to the second electrode portion 33. The first electrode portion 32 includes first electrode ring portions 35A to 35C. The first electrode ring portion 35A is placed on the distal direction side of the piezoelectric element 31A, and the first electrode ring portion 35B is placed between the piezoelectric element 31B and the piezoelectric element 31C in the longitudinal axial direction parallel to the longitudinal axis C. Furthermore, the first electrode ring unit 35C is placed on the proximal direction side of the piezoelectric element 31D. The transducer mounting portion 27 is inserted through the respective first electrode ring portions 35A to 35C.

The second electrode portion 33 includes second electrode ring portions 37A and 37B. The second electrode ring portion 37A is placed between the piezoelectric element 31A and the piezoelectric element 31B in the longitudinal axial direction parallel to the longitudinal axis C. Moreover, the second electrode ring portion 37B is placed between the piezoelectric element 31C and the piezoelectric element 31D in the longitudinal axial direction. The vibrator mounting unit 27 is inserted through the respective second electrode ring portions 37A and 37B.

With the above-described configuration, the piezoelectric element 31A is held between the first electrode ring portion 35A and the second electrode ring portion 37A, and the piezoelectric element 31B is sandwiched between the second electrode ring portion 37A and the first electrode ring portion 35B. Additionally, the piezoelectric element 31C is held between the first electrode ring portion 35B and the second electrode ring portion 37B, and the piezoelectric element 31D is held between the second electrode ring portion 37B and the first electrode ring portion 35C. Thus, the respective piezoelectric elements 31A to 31D are held between the first electrode portion 32 and the second electrode portion 33.

Further, the ultrasonic transducer 22 includes insulation rings 38A and 38B. The insulation ring 38A is placed on the distal direction side of the first electrode ring portion 35A of the first electrode portion 32. The insulation ring 38B is placed on the proximal direction side of the first electrode ring portion 35C of the first electrode portion 32. The transducer mounting portion 27 is inserted through the respective insulation rings 38A and 38B. Furthermore, the ultrasonic transducer 22 includes a back mass 36. The back mass 36 is placed on the proximal direction side of the insulation ring 38B. The piezoelectric elements 31A to 31D, the first electrode portion 32, the second electrode portion 33, and the insulation rings 38A and 38B are pressed toward the distal direction by the back mass 36. Consequently, the piezoelectric elements 31A to 31D, the first electrode portion 32, the second electrode portion 33, and the insulation rings 38A and 38B are held between the horn member 23 and the back mass 36.

FIG. 5 is a view showing an electrical path through which the vibration generating electric power P and the high-frequency electric power P output from the electric power source 26 are supplied. As shown in FIG. 5, the ultrasonic electric power output section 61 of the electric power source 26 is electrically connected to the first electrode portion 32 through the electrical wiring portion 25A. Furthermore, the ultrasonic electric power output section 61 is electrically connected to the second electrode portion 33 through the electrical wiring portion 25B. When the vibration generating electric power P is output from the ultrasonic electric power output section 61, a vibration generating voltage V is applied between the first electrode portion 32 and the second electrode portion 33. When the vibration generating voltage V is applied, a vibration generating current I flows through the piezoelectric elements 31A to 31D sandwiched between the first electrode portion 32 and the second electrode portion 33. That is, on the basis of the vibration generating electric power P from the ultrasonic electric power output section 61 of the electric power source 26, the vibration generating current I is supplied from the ultrasonic electric power output section 61 to the ultrasonic transducer 22. The vibration generating current I is an alternating current whose current direction periodically changes. Furthermore, an ultrasonic impedance value Z which is an impedance value of the vibration generating electric power P is as represented by Expression (1).

[Expression 1]

$$Z = V/I = V^2/P \qquad (1)$$

As shown in FIG. 2, the sheath 8 includes a movable tubular portion 63 made of a conductive material. The movable tubular portion 63 is coupled with the movable handle 13 inside the tubular case portion 11. When the movable handle 13 is opened or closed relative to the fixed handle 12, the movable tubular portion 63 moves relative to the tubular case portion 11 and the ultrasonic probe 9 along the longitudinal axis C. The movable tubular portion 63 is coupled with the vibrator case 21 in a state where it is inserted into the transducer case 21. However, the movable tubular portion 63 is movable relative to the transducer case 21 along the longitudinal axis C.

FIG. 6 and FIG. 7 are views showing configurations of the treatment section 17 and the jaw 18. As shown in FIG. 6, the jaw 18 is attached to the distal portion of the sheath 8 through a fulcrum pin 65. Further, the movable tubular portion 63 is extended up to the distal portion of the sheath 8 along the longitudinal axis C. A distal portion of the movable tubular portion 63 is connected to the jaw 18 through a connection pin 66. When the movable tubular portion 63 moves along the longitudinal axis C by an opening operation or a closing operation of the movable handle 13, the jaw 18 turns around the fulcrum pin 65. Consequently, the jaw 18 pivots to the sheath 8, and the jaw 18 opens or closes relative to the treatment section 17. Here, FIG. 6 shows a state where the jaw 18 is opened relative to the treatment section 17, and FIG. 7 shows a state where no treated target is present between the jaw 18 and the treatment section 17 and the jaw 18 is closed relative to the treatment section 17. Further, FIG. 7 shows a cross section perpendicular to the longitudinal axis C.

As shown in FIG. 6 and FIG. 7, the jaw 18 includes a jaw main body 41 whose proximal portion is attached to the sheath 8, and a grasping member (electrode member) 42 attached to the jaw main body 41. The jaw main body 41 and the grip member 42 are formed of, e.g., a metal having electrical conductivity. Additionally, the jaw 18 includes a pad member 43 attached to the grasping member (electrode member) 42. The pad member 43 is made of, e.g., PTFE having electrical insulation properties.

An abutment portion (an abutment surface) 45, which is abutable with the treatment section 17 in a state where the jaw 18 is closed relative to the treatment section 17, is formed on the pad member 43. When the jaw 18 is closed relative to the treatment section 17 in a state where no treated target is present between the jaw 18 and the treatment section 17, the abutment portion 45 of the pad member 43 comes into contact with the treatment section 17. The contact portion 45 is opposed to the treatment section 17. Moreover, in this embodiment, the abutment portion 45 is perpendicular to an opening direction (a direction of an arrow A1 in each of FIG. 7 and FIG. 8) and a closing direction (a direction of an arrow A2 in each of FIG. 7 and FIG. 8) of the jaw 18.

Here, two directions which are perpendicular (transverse) to the longitudinal axis C and also perpendicular to the opening and closing directions of the jaw 18 are defined as a first width direction (a direction of an arrow B1 in FIG. 8) and a second width direction (a direction of an arrow B2 in FIG. 8). An inclined facing portion 46A that faces the treatment section 17 in a state where it is inclined relative to the contact portion 45 is formed on the first width direction side of the contact portion 45 by the grasp member 42. Further, an inclined facing portion 46B opposed to the treatment section 17 in a state where it is inclined relative to the abutment portion 45 is formed on the second width direction side of the contact portion 45 by the griping member 42. In a state where the contact portion 45 is in abutment with the treatment section 17, the inclined facing portions 46A and 463 are apart from the treatment section 17. Thus, in a state where the contact portion 45 is in contact with the treatment section 17, the grasp member 42 does not come into contact with the treatment section 17.

As shown in FIG. 2 and FIG. 3, one end of an electrical wiring portion 67A, which is different from the electrical wiring portions 25A and 25B, is connected to the proximal portion of the horn member 23. The electrical wiring portion 67A is extended through the inside of the cable 7, and the other end is connected to the high-frequency electric power output section 62 of the electric power source 26. The treatment section 17 is electrically connected to the high-frequency electric power output section 62 through the electrical wiring portion 67A, the horn member 23, and the ultrasonic probe 9. That is, the electrical wiring portion 67A, the horn member 23, and the ultrasonic probe 9 form a probe-side high-frequency path K1 shown in FIG. 5 between the treatment section 17 and the high-frequency electric power output section 62.

A case conductive portion 68 is provided in the transducer case 21. One end of an electrical wiring portion 67B, which is different from the electrical wiring portions 25A, 25B, and 67A, is connected to a proximal portion of the case conductive portion 68. The electrical wiring portion 67B is extended through the inside of the cable 7, and the other end is connected to the high-frequency electric power output section 62 of the electric power source 26. Furthermore, the movable tubular portion 63 of the sheath 8 is constantly in contact with a distal portion of the case conductive portion 68 irrespective of a moving state of the movable tubular portion 63 along the longitudinal axial direction parallel to the longitudinal axis C. Thus, the grasping member (the electrode member) 42 of the jaw 18 is electrically connected to the high-frequency electric power output section 62 through the electrical wiring portion 67B, the case conductive portion 68, the movable tubular portion 63, and the jaw main body 41. That is, the electrical wiring portion 67B, the case conductive portion 68, the movable tubular portion 63, and the jaw main body 41 constitute a jaw-side high-frequency path K2 between the high-frequency electric power output section 62 and the holding member 42. It is to be noted that the probe-side high-frequency path K1 is electrically insulated from the jaw-side high-frequency path K2 in a state where no treated target is griped between the treatment section 17 and the jaw 18.

The treatment section 17 functions as a probe electrode portion (an electrode). As shown in FIG. 5, the high-frequency electric power P' is transmitted (supplied) to the treatment section 17 from the high-frequency electric power output section 62 of the electric power source 26 through the probe-side high-frequency path K1. Moreover, the griping member (an electrode member) 42 of the jaw 18 functions as a jaw electrode portion (an electrode) which is different from the probe electrode portion. The high-frequency electric power P' is transmitted (supplied) to the grasping member 42 of the jaw 18 from the high-frequency electric power output section 62 through the jaw-side high-frequency path K2. When the high-frequency electric power P' is output from the high-frequency electric power output section 62, a high-frequency voltage V' is applied between the treatment section (the probe electrode portion) 17 and the grasping member (the jaw electrode portion) 42. When the high-frequency voltage V' is applied, in a state where the treated target is grasped between the treatment section 17 and the jaw 18, a high-frequency current I' flows through the treated target. That is, on the basis of the high-frequency electric power P' from the high-frequency electric power output section 62, the high-frequency current I' flows between the treatment section (the probe electrode portion) 17 and the clamping member (the jaw electrode unit) 42. The high-frequency current I' is an alternating current whose current direction periodically changes. Additionally, a high-frequency impedance value Z' which is an impedance value of the high-frequency electric power P' is as represented by Expression (2).

[Expression 2]

$$Z'=V'/I'=V'^2/P' \qquad (2)$$

As shown in FIG. 3, the control unit 3 includes a control section 51 which is electrically connected to the electric power source 26. A switch portion 47 is provided inside the fixed handle 12. Opened and closed states of the switch portion 47 are changed over on the basis of an input of an energy operation using the energy operation input button 16. The switch portion 47 is connected to the controller 51 via a signal path portion 48 extended through the transducer case 21 and the inside of the cable 7. When the switch portion 47 is closed, an operation signal is transmitted to the control section 51 through the signal path portion 48. The control section 51 includes an ultrasonic control section 59 and a high-frequency control section 69. The ultrasonic control section 59 is configured to control an output state of the vibration generating electric power P from the electric power source 26 on the basis of the transmitted operation signal. Further, the high-frequency control section 69 is configured to control an output state of the high-frequency electric power P' from the electric power source 26 on the basis of the transmitted operation signal.

Furthermore, the control unit 3 includes an impedance detecting section 52 electrically connected to the electric power source 26 and the control section 51, and a peak detecting section 53 electrically connected to the impedance detecting section 52 and the control section 51. In a state where the vibration generating electric power P is output from the electric power source 26, the impedance detecting section 52 detects the ultrasonic impedance value Z of the vibration generating electric power P with time. Furthermore, the impedance detecting section 52 may detect the high-frequency impedance value Z' of the high-frequency electric power P with time in addition to the ultrasonic impedance value Z. The peak detecting section 53 detects a peak of the ultrasonic impedance value Z (a target peak) on the basis of changes with time of the detected ultrasonic impedance value Z. The peak detecting section 53 includes a gradual decrease detecting sectors 55, a tentative peak value holding section 56, and a peak judging section 57. Details of the gradual decrease detecting section 55, the tentative peak value holding section 56, and the peak judging section 57 will be described later. It is to be noted that the impedance detecting section 52 is, e.g., a detection circuit. Moreover, each of the control section 51 and the peak detecting section 53 is formed of, e.g., a processor including a CPU (Central Processing Unit) or an ASIC (application specific integrated circuit) or a logic circuit such as an FPGA (Field Programmable Gate Array), and a memory (a storage section). Additionally, the control unit 3 includes a notifying section 58 such as a buzzer or a lamp. The notifying section 58 is electrically connected to the control section 51. Details of the notifying section 58 will be described later. Furthermore, an explanation of the target peak and a detection method of the target peak will be also described later.

A function and an effect of the grasping treatment apparatus (ultrasonic treatment apparatus) 1 will now be described later. At the time of giving a treatment to a treated target such as a biological tissue by using the grasping treatment system 1, the sheath 8, the ultrasonic probe 9, and the jaw 18 are inserted into a body or the like in which a treated target is present. Further, the treatment section 17 and the jaw 18 are moved until the treated target is placed between the jaw 18 opened relative to the treating section 17 and the treatment section 17. Furthermore, when the movable handle 13 is closed relative to the fixed handle 12, the treated target is grasped between the treatment section 17 and the jaw 18.

In this state, an energy operation is input by the energy operation input button 16, an operation signal is transmitted to the control section 51, and output of the vibration generating electric power P from the electric power source 26 begins. When the vibration generating electric power P is supplied, the vibration generating current I is converted into an ultrasonic vibration by the piezoelectric elements 31A to 31D. The ultrasonic vibration generated by the ultrasonic transducer 22 is transmitted to the treatment section 17 through the horn member 23 and the ultrasonic probe 9, and the treatment section 17 longitudinally vibrates. When the treatment section 17 longitudinally vibrates in a state where the treated target is griped between the treatment section 17 and the jaw 18, frictional heat is generated between the treated target and the treatment section 17. The frictional heat enables coagulating and simultaneously incising the treated target.

Moreover, when an operation signal based on input of an energy operation is transmitted to the control section 51, an output of the high-frequency electric power P' from the high-frequency electric power output section 62 of the electric power source 26 is started. When the high-frequency electric power P' is transmitted (supplied) to the treatment section 17, the treatment section 17 functions as the probe electrode portion. Additionally, when the high-frequency electric power P' is transmitted (supplied) to the grasping member 42 of the jaw 18, the griping member 42 functions as the jaw electrode portion. Thus, the high-frequency current I' flows through the treated target grasped between the treatment section 17 and the jaw 18. The treated target is coagulated or incised by the high-frequency current I'.

When a treatment is given to the treated target held between the treatment section 17 and the jaw 18, cut-and-divided of the treated target occurs in at least a part range of the treated target in the transmitting direction of the ultrasonic vibration. FIG. 8 is a view for explaining the cut-and-divided of the treated target H grasped between the treatment section 17 and the jaw 18. It is to be noted the cut-and-divided occurs over the entire range of the treated target in the transmitting direction (the longitudinal axial direction) of the ultrasonic vibration in some cases, or it occurs only in a part range of the treated target in the transmitting direction (the longitudinal axis direction) of the ultrasonic vibration in some cases. In a region where the cutoff has occurred, the treated target H is divided at a dividing face D that is parallel to the transmitting direction of the ultrasonic vibration and also parallel to the opening and closing directions of the jaw (a direction of an arrow A1 in FIG. 8 and a direction of an arrow A2 in FIG. 8). The dividing face D is perpendicular to the first width direction (a direction of an arrow 31 in FIG. 8) and a second width direction (a direction of an arrow B2 in FIG. 8). Thus, in the range where the cut-and-divided has occurred, the treated target H is divided into a region H1 on the first width direction side of the dividing face D and a region H2 on the second width direction side of the dividing face D.

In the range where the treated target H is divided by the cut-and-divided, the contact portion 45 of the jaw 18 comes into contact with the treatment section 17. When the abutment portion 45 of the jaw 18 vibrates (longitudinally vibrates) by the ultrasonic vibration in a state where it is in contact with the treatment section 17, the contact portion 45 of the jaw 18 is worn. Thus, it is important to appropriately judge whether the treated target H has been cut-and-divided. When the cut-and-divided occurs only in a part range of the treated target H in the transmitting direction (the longitudinal axis direction) of the ultrasonic vibration, the cut-and-divided does not occur in a remaining part of range of the treated target H in the transmitting direction of the ultrasonic vibration.

Here, the ultrasonic impedance value Z of the vibration generating electric power P changes in accordance with a load to the ultrasonic probe 9, i.e., a load to the ultrasonic transducer 22 connected to the ultrasonic probe 9. FIG. 9 shows an example of changes with time in an ultrasonic impedance value Z from an output start of the vibration generating electric power P from the electric power source 26. In FIG. 9, an axis of ordinate represents the ultrasonic impedance value Z, and an axis of abscissa represents an elapsed time t from an output start of the vibration generating electric power P. Pressing force to the treatment section 17 from the jaw 18 gradually increases up to the vicinity of a time point at which the treated target H is cut-and-divided due to, e.g., changes in a state of the treated target H between the contact portion 45 of the jaw 18 and the treatment section 17. In this reason, the load to the ultrasonic probe 9 gradually increases. Thus, the ultrasonic impedance value Z gradually increases with time until the treatment target H is cut-and-divided. Here, the term of the gradual increase with time means that the ultrasonic impedance value Z gradually increases as the elapsed time t advances, and it also includes that the ultrasonic impedance value Z gradually increases while including a small increase or decrease of tens of Ω or less.

When the treated target H is cut-and-divided, since the contact portion 45 of the jaw 18 is placed near the treatment section 17, a surface of the pad member 43 (the abutment portion 45) denatures due to frictional heat generated by the ultrasonic vibration of the treatment section 17. Thus, the load to the ultrasonic probe 9 is gradually decreased. Therefore, the ultrasonic impedance value Z gradually decreases subsequent to the vicinity of the time point where the treated target H is cut off. Here, gradually decreasing with time means that the ultrasonic impedance value Z gradually decreases as the elapsed time t advances, and it also includes that the ultrasonic impedance value Z gradually decreases while including a small increase or decrease of tens of Ω or less.

Since the ultrasonic impedance value Z changes due to the cut-and-divided as described above, the ultrasonic impedance value Z becomes a peak (a maximal value) with time in the vicinity of a time point when the treated target H is cut-and-divided (for example, in the vicinity of a time point when the abutment portion 45 of the jaw 18 begins to come into contact with the treatment section 17). When the time-dependent peak of the ultrasonic impedance value Z is detected, it can be appropriately judged whether the treated target H has been cut-and-divided. Here, in the example shown in FIG. 9, an ultrasonic impedance value Z1 becomes a target peak which is a peak (peak value) caused due to the cut-and-divided of the treated target H. Further, an elapsed time t1 is a target peak point at which the target peak is produced.

FIG. 10 is a view (a flow) showing an actuating state of the control unit 3 from start of the output of the vibration generating electric power P and the output of the high-frequency electric power P'. Further, FIG. 11 shows changes with time of an amplitude U of the ultrasonic vibration in the treatment section 17 (e.g., the distal end of the ultrasonic probe 9) in an example where the ultrasonic impedance value Z changes with time as shown in FIG. 9. Furthermore, FIG. 12 shows changes with time of the high-frequency current I' flowing through a treated target H in the example where the ultrasonic impedance value Z changes with time as shown in FIG. 9. In FIG. 11, an axis of ordinate represents the amplitude U of the ultrasonic vibration, and an axis of abscissa represents an elapsed time t from the start of the output of the vibration generating electric power P. In FIG. 12, an axis of ordinate represents the high-frequency current I', and an axis of abscissa represents an elapsed time t from the start of the output of the high-frequency electric power P' (the start of the output of the vibration generating electric power P).

As shown in FIG. 10, in a treatment, the output of the high-frequency electric power P' is started from the high-frequency electric power output section 62 in a first high-frequency output mode (a step S102) simultaneously with the start of the output of the vibration generating electric power P from the ultrasonic electric power output section 61 of the electric power source 26 in a first ultrasonic output mode (a step S101). In this embodiment, in the first ultrasonic output mode, the ultrasonic control section 59 controls an output state of the vibration generating electric power P in constant-current control where an effective value (a current value) of the vibration generating current (the alternating current) I is maintained at a fixed first current value I1. Thus, the vibration generating electric power P (the vibration generating voltage V) is adjusted in accordance with a change in the ultrasonic impedance value Z so that the vibration generating current I becomes the constant first current value I1.

Here, the amplitude U of the ultrasonic vibration of the treatment section 17 is proportionate to the effective value (the current value) of the vibration generating current I. In the first ultrasonic output mode, since the vibration generating current I is maintained at the first current value I1, the treatment section 17 vibrates with a fixed first amplitude U1 as shown in FIG. 11. It is to be noted that in any other region than the treatment section 17 (e.g., the proximal end of the ultrasonic probe 9 or the horn member 23), the amplitude of the ultrasonic vibration is proportionate to the effective value of the vibration generating current I.

Moreover, as shown in FIG. 12, according to this embodiment, in the first high-frequency output mode, the high-frequency control section 69 controls an output state of the high-frequency electric power P' into a state of performing intermittent output where the high-frequency electric power P' is intermittently output from the high-frequency electric power output section 62. Thus, in the first high-frequency output mode, the output state of the high-frequency electric power P' from the electric power source 26 is periodically modulated (changed) between an output stage ΔS'1 where the high-frequency power P' is output and a non-output stage ΔS'2 where the high-frequency power P' is not output. That is, in the first high-frequency output mode, the output state of the high-frequency power P' periodically changes in a modulation cycle (a high-frequency modulation cycle) ΔW'. In the example shown in FIG. 12, the output state of the high-frequency power is modulated in a modulation cycle ΔW'1.

In the first high-frequency output mode, during the output stage ΔS'1, the high-frequency current (the alternating current) I' whose amplitude (a crest value) I'pp becomes a first amplitude I'pp1 flows through the treated target H grasped between the treatment section 17 and the jaw 18. Additionally, during the output stage ΔS'1, the high-frequency power P' (the high-frequency current I') is output in an output cycle Δω'. Here, the output cycle Δω' corresponds to an elapsed time from a peak to a next peak (from a trough to a next trough) of a waveform of the high-frequency current I' in the output stage ΔS'1. In the example shown in FIG. 12, during the output stage ΔS'1 in the first high-frequency output mode, the high-frequency electric power P' is output in the output cycle Δω'1.

Since the high-frequency electric power P' is output as described above, in the first high-frequency output mode, an effective value (a current value) I'rms of the high-frequency current I' flowing through the treated target H in the output stage ΔS'1 is a first effective value I'rms1. That is, in the first high-frequency output mode, the high-frequency electric power P' (the high-frequency voltage V') is adjusted so that the high-frequency current I' has the first effective value I'rms1 in the output stage ΔS'1. Further, in the first high-frequency output mode, a wave number n of the high-frequency current I' in one output stage ΔS1 is 3.

When the output of the vibration generating electric power P in the first ultrasonic output mode and the output of the high-frequency electric power P in the first high-frequency output mode are started, the impedance detecting section 52 begins detection of the ultrasonic impedance value Z of the vibration generating electric power P with time (a step S103). Consequently, the ultrasonic impedance value Z is detected with time. According to this embodiment, in the first ultrasonic output mode, to maintain the amplitude of the ultrasonic vibration in the treatment section 17 at the constant first amplitude U1, the constant-current control that allows the vibration generating current I to have the fixed first current value I1 is performed. Thus, changes with time of at least one of the vibration generating electric power P and the vibration generating voltage V are detected, and the ultrasonic impedance value Z is calculated on the basis of the detected vibration generating electric power P and/or vibration generating voltage V with the use of Expression (1). Consequently, the ultrasonic impedance value Z is detected with time. It is to be noted that the high-frequency impedance value Z' may be detected with time in addition to the ultrasonic impedance value Z. Further, in a given example, the impedance detecting section 52 detects the vibration generating voltage V and the vibration generating current I with time, and calculates the ultrasonic impedance value Z by using Expression (1).

Furthermore, the peak detecting section 53 performs detection processing of a target peak of the ultrasonic impedance value Z produced due to cut-and-divided of the treated target H on the basis of the changes with time of the ultrasonic impedance value Z (a step S104). At this time, a target peak point at which the ultrasonic impedance value Z becomes a target peak (a target peak value) may be detected.

Figure 13:
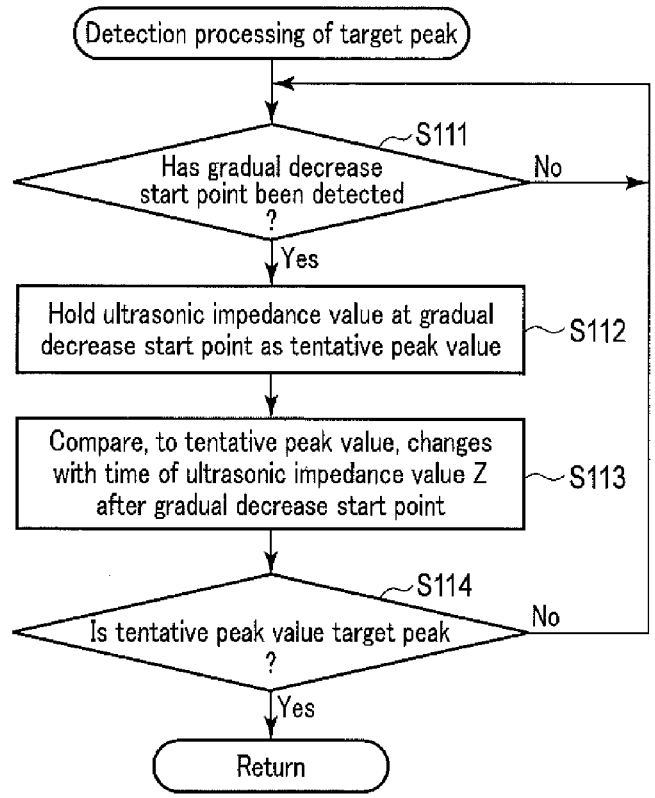
FIG. 13 is a flowchart showing detection processing of a target peak performed by a peak detecting section according to the first embodiment.

FIG. 13 is a view showing the detection processing of the target peak performed by the peak detecting section 53 (the step S104 in FIG. 10). That is, FIG. 13 shows a method of detecting the target peak by the peak detecting section 53. As shown in FIG. 13, in the detection processing of the target peak, the gradual decrease detecting section 55 first detects a gradual decrease start point at which the ultrasonic impedance value Z starts to gradually decrease on the basis of a detection result of the ultrasonic impedance value Z in the impedance detecting section 52 (a step S111). In the example shown in FIG. 9, an elapsed time t1 is detected as the gradual decrease start point. When the gradual decrease start point is detected (the step S111—Yes), the tentative peak value holding section 56 holds the ultrasonic impedance value Z at the detected gradual decrease start point as a tentative peak value (a step S112). In the example shown in FIG. 9, the ultrasonic impedance value Z1 at the elapsed time t1 is held as the tentative peak value.

Furthermore, the peak judging section 57 executes comparison processing of changes with time of the ultrasonic impedance value after the gradual decrease start point relative to the held tentative peak value (a step S113). In the example shown in FIG. 9, changes with time of the ultrasonic impedance value Z after the elapsed time t1 are compared relative to the ultrasonic impedance value Z1 held as the tentative peak value. Moreover, based on the comparison of the changes with time of the ultrasonic impedance value Z relative to the tentative peak value, the peak judging section 57 judges whether the tentative peak value is the target peak caused due to the cut-and-divided of the treated target H (a step S114). In the example shown in FIG. 9, a judgment is made upon whether the ultrasonic impedance value Z1 held as the tentative peak value is the target peak (the target peak value). At this time, whether the detected gradual decrease start point is a target peak point may be judged. In the example shown in FIG. 9, the elapsed time t1 which is the gradual decrease start point is judged to be the target peak point at a time point which is the elapsed time t1+ΔT1.

In a given example, at the step S113 (the comparison processing) in FIG. 13, whether a decrement εreal of the ultrasonic impedance value Z from the tentative peak value is equal to or higher than a reference decrement ε after elapse of a reference time ΔT from the gradual decrease start point is determined by comparison. Additionally, whether the ultrasonic impedance value Z continuously falls below the tentative peak value after the gradual decrease start point is determined by comparison at the step S113. In this example, when the decrement εreal of the ultrasonic impedance value Z from the tentative peak value is equal to or higher than the reference decrement ε after elapse of the reference time ΔT from the gradual decrease start point and the ultrasonic impedance value Z continuously falls below the tentative peak value, the tentative peak value is determined to be the target peak. In the example shown in FIG. 9, after the gradual decrease start point t1, the ultrasonic impedance value Z continuously falls below the tentative peak value Z1. Further, a decrement ε1 real of the ultrasonic impedance value Z during elapse of a reference time ΔT1 from the elapsed time t1 which is the gradual decrease start point is equal to or higher than a reference decrement ε1. Thus, in the example shown in FIG. 9, the peak judging section 57 determines that the tentative peak value Z1 is the target peak. Therefore, at a time point of the elapsed time t1+ΔT1 (in fact immediately after the elapsed time t1+ΔT1), it is determined that at least a part of the treatment target H has been cut and divided at a time point of the elapsed time t1 (a time point when the tentative peak value Z1 was detected).

Furthermore, in another example, at the step S113, whether the ultrasonic impedance value Z gradually increases after the gradual decrease start point may be judged. Moreover, when the ultrasonic impedance value Z gradually increases after the gradual decrease start point, whether an increment ξ real of the ultrasonic impedance value Z from a gradual increase start point at which gradual increase begins is equal to or higher than a reference increment ξ is judged at the step S113. In this example, when the decrement εreel of the ultrasonic impedance value Z from the tentative peak value is equal to or higher than the reference decrement ε after elapse of the reference time ΔT from the gradual decrease start point and the increment ξreal of the ultrasonic impedance value Z from the gradual increase start point does not become equal to or higher than the reference increment ξ, the tentative peak value is determined to be the target peak. In the example shown in FIG. 9, after the gradual decrease start point t1, the ultrasonic impedance value Z does not gradually increase. Additionally, the decrement ε1 real of the ultrasonic impedance value Z during elapse of the reference time ΔT1 is equal to or higher than the reference decrement ε1 without increasing beyond the reference increment ξ from the elapsed time t1 which is the gradual decrease start point. Thus, in the example shown in FIG. 9, at a time point of the elapsed time t1+ΔT1 (in fact immediately after the elapsed time t1+ΔT1), the peak judging section 57 determines that the tentative peak value Z1 is the target peak.

It is to be noted that, in the foregoing example, a length of the reference time ΔT, a magnitude of the reference decrement ε, and a magnitude of the reference increment ξ are not determined as prescribed values, and they may be set in accordance with, e.g., changes with time of the ultrasonic impedance value Z. Thus, values of the reference time ΔT, the reference decrement ε, and the reference increment ξ change depending on situations. Further, the comparison of changes with time of the ultrasonic impedance value after the gradual decrease start point relative to the tentative peak value (the step S113) and the judgement on whether the tentative peak value is the target peak value (the step S114) are not restricted to the foregoing example.

As described above, when the comparison of changes with time of the ultrasonic impedance value after the gradual decrease start point relative to the tentative peak value (the step S113) and the judgement on whether the tentative peak value is the target peak value (the step S114) are carried out, the target peak caused by the cut-and-divided of the treated target H is detected. The target peak is detected after elapse of the reference time ΔT from the target peak point. Thus, a peak detection point at which the target peak is detected is a time point after the target peak point, and the target peak is not detected at the target peak point at which the ultrasonic impedance value Z reaches the target peak. In the example shown in FIG. 9, the elapsed time t1+ΔT1 is the peak detection point at which the target peak is detected.

For example, when the treated target H is thick (a dimension of the treated target H is large in the opening and closing directions of the jaw 18), a peak of the ultrasonic impedance value Z is produced at a moment when the contact portion 45 of the jaw 18 comes into contact with the treated target H and a contact surface of the treated target H to the jaw 17 starts to be incised. In this embodiment, since the detection of the target peak is executed described above, it is determined that the peak produced due to the contact of the contact portion 45 with the treated target H has not been the target peak. Thus, when the peak different from the target peak is produced before the target peak, the target peak is accurately detected.

When the peak produced due to the cut-and-divided of the treated target H is detected in accordance with the flow shown in FIG. 10 (the steps S101 to S104), the ultrasonic control section 59 switches an output state of the ultrasonic electric power P from the ultrasonic electric power output section 61 of the electric power source 26 from the first ultrasonic output mode to the second ultrasonic output mode (a step S105). Thus, in the second ultrasonic output mode, the vibration generating electric power P is output. In this embodiment, after the peak detection point at which the target peak is detected (a point at which the target peak is determined by the peak determination) or preferably immediately after the target peak determination point, the first ultrasonic output mode is switched to the second ultrasonic output mode. Thus, on the basis of the detection of the target peak, at the same time of or after the peak detection point (the target peak judgment point), switching to the second ultrasonic output mode is performed. In an example shown in FIG. 11 (FIG. 9), the first ultrasonic output mode is switched to the second ultrasonic output mode at a peak detection point t1+ΔT1.

According to this embodiment, in the second ultrasonic output mode, the ultrasonic control section 59 controls the output state of the vibration generating electric power P on the basis of the constant-current control which maintains the effective value (the current value) of the vibration generating current I at a fixed second current value smaller than the first current value I1. Thus, the vibration generating electric power P (the vibration generating voltage V) is adjusted in accordance with a change in the ultrasonic impedance value so that the vibration generating current I has the constant second current value I2. As described above, the amplitude U of the ultrasonic vibration in the treatment section 17 is proportionate to the effective value of the vibration generating current I. In the second ultrasonic output mode, since the vibration generating current I is maintained at the second current value I2, as shown in FIG. 11, the treatment section 17 vibrates with a fixed second amplitude U2 smaller than the first amplitude U1. A ratio of the second amplitude U2 to the first amplitude U1 is, e.g., 20% to 80%. Since the amplitude of the treatment section 17 is adjusted as described above in the first ultrasonic output mode and the second ultrasonic output mode, when an average of the amplitudes U of the treatment section 17 provided by the ultrasonic vibration during a predetermined unit time is an average amplitude Uave, the average amplitude Uave of the treatment section 17 during the predetermined unit time in the second ultrasonic output mode is smaller than that in the first ultrasonic output mode. It is to be noted that the amplitude U of the treatment section 17 changes by adjusting the electric power value of the vibration generating electric power P, the effective value (the current value) of the vibration generating current I, and others.

Here, assuming that a vibration velocity of the treatment section 17 provided by the ultrasonic vibration is v and a resonance frequency of the ultrasonic vibration is F, Expression (3) is achieved.

[Expression 3]

$$v \propto U \cdot F \quad (3)$$

That is, the vibration velocity v is proportionate to a product of the amplitude U and the resonance frequency F. As described above, the second amplitude U2 of the treatment section 17 in the second ultrasonic output mode is smaller than the first amplitude U1 of the treatment section 17 in the first ultrasonic output mode. Thus, assuming that an average of the vibration velocities v of the treatment section 17 provided by the ultrasonic vibration during a predetermined unit time is an average vibration velocity vave, the average vibration velocity vave of the treatment section 17 during the predetermined unit time in the second ultrasonic output mode is smaller than that in the first ultrasonic output mode.

When the average vibration velocity vave of the treatment section 17 during the predetermined unit becomes small, a heat quantity of frictional heat generated by the vibration of the treatment section 17 in a treatment for the treated target H is reduced. When the heat quantity of the frictional heat is reduced, incision performance provided by the ultrasonic vibration of the treatment section 17 is decreased in the treatment for the treated target E. Thus, the incision performance provided by the ultrasonic vibration of the treatment section 17 in the second ultrasonic output mode is smaller than that in the first ultrasonic output mode before the peak detection point.

When a peak produced due to cutoff of the treated target H is detected in accordance with the flow shown in FIG. 10 (the steps S101 to S104), the high-frequency control section 69 switches an output state of the high-frequency electric power P' from the high-frequency electric power output section 62 of the electric power source 26 from the first high-frequency output mode to the second high-frequency output mode (a step S106) simultaneously with the switching of the output state of the vibration generating electric power P by the ultrasonic control section 59 (the step S105). Thus, in the second high-frequency output mode, the high-frequency electric power P' is output. In this embodiment, at the peak detection point when the target peak is detected (the target peak determination point), the first high-frequency output mode is switched to the second high-frequency output mode. Thus, on the basis of the detection of the target peak, at the same time of or after the peak detection point (the target peak determination point), switching to the second high-frequency output mode is performed. In an example shown in FIG. 13 (FIG. 9), the first high-frequency output mode is switched to the second high-frequency output mode at the peak detection point t1+ΔT1.

As shown in FIG. 12, according to this embodiment, in the second high-frequency output mode, like the first high-frequency output mode, intermittent output that the high-frequency power P' is intermittently output from the high-frequency electric power output section 62 is performed. Thus, in the second high-frequency output mode, likewise, the output state of the high-frequency electric power P' from the electric power source 26 is periodically modulated (changed) in a modulation cycle (a high-frequency modulation cycle) ΔW' between the output stage ΔS'1 where the high-frequency electric power P' is output and the non-output stage ΔS'2 where the high-frequency electric output P' is not output. In the example shown in FIG. 12, in the second high-frequency output mode, the output state of the high-frequency electric power is modulated in a modulation cycle ΔW'1. Further, in the second high-frequency output mode, like the first high-frequency output mode, the high-frequency electric power P' is output in an output cycle Δω' (Δω'1) during the output stage ΔS'1, and a wave number n of the high-frequency current I' in one output stage ΔS1 is 3.

However, in the second high-frequency output mode, in the output stage ΔS'1, an amplitude (a crest value) I'pp of the high-frequency current I' flowing through the treated target H grasped between the treatment section 17 and the jaw 18 is a second amplitude I'pp2 larger than the first amplitude I'pp1. Thus, in the second high-frequency output mode, the effective value (the current value) I'rms of the high-frequency current I' in the output stage ΔS'1 is a second effective value I'rms2 larger than the first effective value I'rms1. That is, according to this embodiment, in the second high-frequency output mode, when the amplitude (the crest value) I'pp of the high-frequency current I' is increased beyond that in the first high-frequency output mode, the effective value I'rms of the high-frequency current I' becomes higher than that in the first high-frequency output mode. Here, according to Expression (2), the amplitude I'pp of the high-frequency current I' varies when a voltage value of the high-frequency voltage V' applied between the treatment section (the probe electrode portion) 17 and the grasping member (the jaw electrode portion) 42 and an electric power value of the high-frequency electric power P' change. Thus, the high-frequency control section 69 adjusts at least one of the voltage value of the high-frequency voltage V' and the electric power value of the high-frequency electric power P' to increase the effective value I'rms of the high-frequency current I' in the second high-frequency output mode beyond that in the first high-frequency output mode. It is to be noted that a ratio of the second effective value I'rms2 to the first effective value I'rms1 is approximately 110% to 130%.

Here, the incision performance of the treated target H provided by the high-frequency current I' (the high-frequency electric power P') varies in accordance with thermal energy (Joule heat) Q' generated by the high-frequency current I' flowing through the treated target H between the treatment section (the probe electrode portion) 17 and the grasping member (the jaw electrode portion) 42. Magnitude of the thermal energy Q' is affected by the effective value I'rms of the high-frequency current I'. That is, when the effective value I'rms of the high-frequency current I' increases, the thermal energy Q' rises.

In the first high-frequency output mode, the first effective value I'rms1 of the high-frequency current I' is small as described above. Furthermore, in the first high-frequency output mode, the intermittent output is performed, and the high-frequency electric power P' is intermittently output with time. Thus, the thermal energy Q' generated by the high-frequency current I' is reduced. When the thermal energy Q' is reduced, the treated target H is not molten by the thermal energy Q' produced by the high-frequency I', and the incision performance provided by the high-frequency current I' is lowered. Thus, in the first high-frequency output mode, the treated target H is not incised by the high-frequency current I', the treated target H is denatured by the high-frequency current I', and coagulation of the treated target H is promoted. It is to be noted that, when the high-frequency electric power P' is output in the first high-frequency output mode, the vibration generating electric power P is output in the first ultrasonic output mode, and the treated target is coagulated and incised at the same time by the frictional heat generated due to the vibration of the treatment section 17.

On the other hand, in the second high-frequency output mode, the second effective value I'rms2 of the high-frequency current I' increases. Thus, in the second high-frequency output mode, the thermal energy Q' produced by the high-frequency current I' becomes large. When the thermal energy Q' becomes large, the treated target H is molten by the thermal energy Q' generated due to the high-frequency current I', and the incision performance provided by the high-frequency current I' is improved. Thus, in the second high-frequency output mode, the treated target H is incised by the high-frequency current I'. It is to be noted that, when the high-frequency electric power P' is output in the second high-frequency output mode, the vibration generating electric power P is output in the second ultrasonic output mode, and the incision performance provided by the ultrasonic vibration is lowered.

Here, even if the treated target H is divided only in a part of a range of the treated target H in a transmitting direction (the longitudinal axial direction) of the ultrasonic vibration, the abutment portion 45 of the jaw 18 comes into contact with the treatment section 17 in the range where the treated target H is divided. Thus, even if the treated target H is cut and divided only in a part of the range of the treated target H in the longitudinal axial direction, a target peak arising from the cut-and-divided is produced. In this case, in a remaining part of the range of the treated target H in the transmitting direction of the ultrasonic vibration, the treated target H is not divided at the peak detection point. Thus, when the output of the vibration generating electric power P and the high-frequency electric power P' from the electric power source 26 is stopped at the peak detection point, a remaining part of the treated target H which is not divided at a dividing face D, which is parallel to the transmitting direction (the longitudinal axis direction) of the ultrasonic vibration and also parallel to the opening-and-closing direction of the jaw 18, is produced in a remaining part of the range of the treatment target H.

Thus, in this embodiment, on the basis of the detection of the target peak, the output state of the high-frequency electric power P' is switched from the first high-frequency output mode to the second high-frequency output mode. As described above, in the second high-frequency output mode, since the thermal energy generated by the high-frequency current I' becomes large, the incision performance provided by the high-frequency current I' grows. Thus, even if the treated target H is not divided in a part of the range at the peak detection point (the target peak determination point), the treated target H is incised by the thermal energy Q' generated due to the high-frequency current I' in an undivided part of the range. Consequently, even in the undivided part of the range at the peak detection point, the treated target H is divided at the dividing face D. As described above, production of an uncut part in the treated target H is effectively prevented.

Further, on the basis of the detection of the target peak, the output state of the vibration generating electric power P is switched from the first ultrasonic output mode to the second ultrasonic output mode. In the second ultrasonic output mode, since the treatment section 17 vibrates with the small second amplitude U2, the average vibration velocity vave of the treatment section 17 during the predetermined unit time is reduced as described above, and the heat quantity of the frictional heat generated by the vibration of the treatment section 17 is lowered. Thus, even if the treatment section 17 vibrates in the second ultrasonic output mode after the peak detection point, wear and thermal deformation of a pad member 43 (the abutment portion 45) are reduced in a region where the abutment portion 45 comes into contact with the treatment section 17.

Furthermore, since the pad member 43 (the contact portion 45) has electrically insulation properties, the high-frequency electric power P' (the high-frequency current I') is not transmitted to the pad member 43 in a state where the high-frequency current I' flows between the treatment section (the probe electrode portion) 17 and the grasping member (the jaw electrode portion) 42. Thus, the pad member 43 is hardly affected by the thermal energy Q' generated by the high-frequency current I'. Therefore, even in the second high-frequency output mode where the thermal energy Q' generated by the high-frequency current I' increases, the thermal deformation of the pad member 43 (the abutment portion 45) provided by the thermal energy Q' can be reduced.

As shown in FIG. 10, when the output state of the vibration generating electric power P from the electric power source 26 is switched to the second ultrasonic output mode (the step S105) and the output state of the high-frequency electric power P' from the electric power source 26 is switched to the second high-frequency output mode (a step S106), the notifying section 58 notifies that the output state of the vibration generating electric power P and the output state of the high-frequency electric power P' have been switched (a step S107). Here, sound is emitted when the notifying section 58 is a buzzer, or lighting is performed when the notifying section 58 is a lamp. An surgeon judges whether the treated target H is cut and divided with the use of the notifying section 58, and also recognizes that the output state of the ultrasonic electric power P has been switched to the second ultrasonic output mode and that the output state of the high-frequency electric power P' has been switched to the second high-frequency output mode. Moreover, the output of the vibration generating electric power P from the ultrasonic electric power output section 61 is stopped (a step S108), and the output of the high-frequency electric power P' from the high-frequency electric power output section 62 is stopped (a step S109). The output of the vibration generating electric power P and the output of the high-frequency electric power P' may be manually stopped by the operator, or it may be automatically stopped after elapse of a predetermined output time $\Delta Y$ from the peak detection point (the start of the output of the vibration generating electric power P in the second ultrasonic output mode, and the start of the output of the high-frequency electric power P' in the second high-frequency output mode). In the example shown in FIG. 11 and FIG. 12, after elapse of a predetermined output time $\Delta Y1$ from a peak detection point $t1+\Delta T1$, the output of the vibration generating electric power P and the output of the high-frequency electric power P' are automatically stopped.

In the grasping treatment apparatus 1 according to this embodiment, the gradual decrease start point of the ultrasonic impedance value Z is detected, and the ultrasonic impedance value at the gradual decrease start point is held as a tentative peak value. Additionally, whether the held tentative peak value is the target peak which is a detection target is judged by comparing changes with time of the ultrasonic impedance value after the gradual decrease start point relative to the tentative peak value. Thus, the target peak can be appropriately detected irrespective of magnitude of the target peak (the target peak value) produced due to the cut-and-divided. Therefore, in the treatment for the treated target H grasped between the treatment section 17 and the jaw 18 using the ultrasonic vibration, whether the treated target H is cut and divided can be appropriately judged.

Further, in this embodiment, on the basis of the detection of the target peak, the output state of the high-frequency electric power P' is switched to the second high-frequency output mode where the thermal energy generated by the high-frequency current I' becomes large. Thus, even if the treated target H is not divided in a part of the range at the peak detection point, the treated target H is incised in an undivided part of the range by the thermal energy Q' generated due to the high-frequency current I'. Consequently, it is possible to effectively prevent the uncut part from being produced in the treated target H.

Furthermore, on the basis of the detection of the target peak, the output state of the vibration generating electric power P is switched to the second ultrasonic output mode where the treatment section 17 vibrates with the small second amplitude U2. Thus, after the peak detection point, a heat quantity of the frictional heat generated by the vibration of the treatment section 17 is reduced. Therefore, even if the treatment section 17 vibrates in the second ultrasonic output mode after the peak detection point, wear and thermal deformation of the pad member (the abutment portion section 45) can be reduced in a region where the contact portion 45 comes into contact with the treatment section 17.

(Modification)

Figure 14:
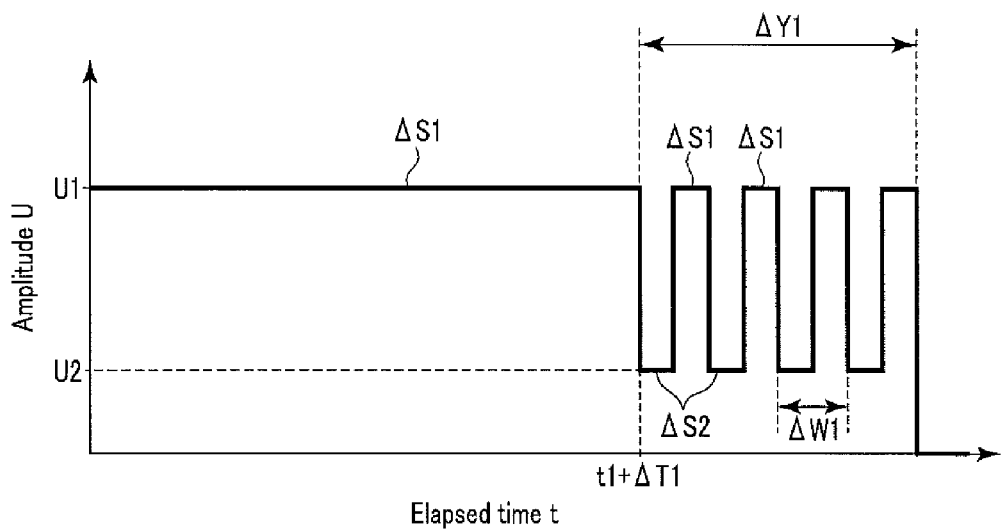
FIG. 14 is a schematic view showing an example of changes with time of the amplitude of the ultrasonic vibration in the treatment section according to a first modification.

It is to be noted that, in the first embodiment, although the amplitude of the treatment section 17 is maintained constant at the second amplitude in the second ultrasonic output mode, it is not restricted thereto. For example, as a first modification, the amplitude U of the ultrasonic vibration in the treatment section 17 (e.g., the distal end of the ultrasonic probe 9) may change with time in the second ultrasonic output mode as shown in FIG. 14. FIG. 14 shows changes with time of the amplitude U of the ultrasonic vibration in the treatment section 17 (e.g., the distal end of the ultrasonic probe 9) in an example where the ultrasonic impedance value changes with time as shown in FIG. 9. In FIG. 14, an axis of ordinate represents the amplitude U of the ultrasonic vibration, and an axis of abscissa represents an elapsed time t from the start of output of the vibration generating electric power P.

Here, a vibration state where the treatment section 17 vibrates with the fixed first amplitude U1 is defined as a first vibration stage $\Delta S1$, and a vibration state where the treatment section 17 vibrates with a fixed second amplitude U2 smaller than the first amplitude U1 is defined as a second vibration stage $\Delta S2$. In this modification, the vibration state of the treatment section 17 is continuously maintained as the first vibration stage $\Delta S1$ in the first ultrasonic output mode. Thus, in the first ultrasonic output mode, the treatment section 17 vibrates with the constant first amplitude U1. Furthermore, in the second ultrasonic output mode, the vibration state provided by the ultrasonic vibration of the treatment section 17 periodically changes between the first vibration stage $\Delta S1$ and the second vibration stage $\Delta S2$. That is, in the second ultrasonic output mode, the vibration state of the treatment section 17 is modulated (changed) in a modulation cycle (a cycle) $\Delta W$. It is to be noted that the modulation cycle (an ultrasonic modulation cycle) $\Delta W$ corresponds to an elapsed time from the start of the first vibration stage $\Delta S1$ to the start of the next first vibration stage $\Delta S1$ (from the start of the second vibration stage $\Delta S2$ to the start of the next second vibration stage $\Delta S2$). In the example shown in FIG. 14, the vibration state of the treatment section 17 changes in the modulation cycle $\Delta W1$ in the second ultrasonic output mode.

As described above, since the output state of the vibration generating electric power P changes between the first ultrasonic output mode and the second ultrasonic output mode, a time ratio $\tau$ of the first vibration stage $\Delta S1$ to the second vibration stage $\Delta S2$ is smaller than that in the first ultrasonic output mode. Since the time ratio $\tau$ of the first vibration stage $\Delta S1$ where the amplitude U of the treatment section 17 increases is reduced, the average amplitude Uave of the treatment section 17 during a predetermined unit time in the second ultrasonic output mode is smaller than that in the first ultrasonic output mode. Thus, on the basis of Expression (3) and others described in the first embodiment, in this modification, likewise, the average amplitude velocity vave of the treatment section 17 during the predetermined unit time in the second ultrasonic output mode is smaller than that in the first ultrasonic output mode.

Since the average vibration velocity vave of the treatment section 17 during the predetermined unit time is reduced, in this modification, likewise, a heat quantity of the frictional heat generated by the vibration of the treatment section 17 in the treatment for the treated target H is decreased in the second ultrasonic output mode. When the heat quantity of the frictional heat is reduced, the incision performance provided by the ultrasonic vibration in the treatment section 17 is lowered in the treatment for the treated target H. Thus, in the second ultrasonic output mode, the incision performance provided by the ultrasonic vibration of the treatment section 17 is smaller than that in the first ultrasonic output mode before the peak detection point.

Further, according to another modification, in the second ultrasonic output mode, the resonance frequency F of the ultrasonic vibration may be decreased to be smaller than that in the first ultrasonic output mode. On the basis of Expression (3), since the resonance frequency F is decreased, the average vibration velocity vave of the treatment section 17 during the predetermined unit time in the second ultrasonic output mode is smaller than that in the first ultrasonic output mode. Thus, in the second ultrasonic output mode, the incision performance provided by the ultrasonic vibration of the treatment section 17 becomes lower than that in the first ultrasonic output mode before the peak detection point.

According to the first embodiment and the foregoing modifications, in the second ultrasonic output mode, the average vibration velocity vave of the treatment section 17 during the predetermined unit time could be lower than that in the first ultrasonic output mode. Consequently, in the second ultrasonic output mode, the incision performance provided by the ultrasonic vibration of the treatment section 17 is lower than that in the first ultrasonic output mode before the peak detection time.

Furthermore, as a second modification, as shown in FIG. 15 and FIG. 16, the output of the vibration generating electric power P may be stopped on the basis of the detection of the target peak. FIG. 15 shows an actuating state of the control unit 3 (a flow) after the start of output of the vibration generating electric power P and output of the high-frequency power P'. FIG. 16 shows changes with time of the amplitude U of the ultrasonic vibration in the treatment section 17 (e.g., the distal end of the ultrasonic probe 9) in an example where the ultrasonic impedance value Z changes with time as shown in FIG. 9. In FIG. 16, an axis of ordinate represents the amplitude U of the ultrasonic vibration, and an axis of abscissa represents an elapsed time t from the start of output of the vibration generating electric power P.

As shown in FIG. 15 and FIG. 16, in this modification, the output of the vibration generating electric power P is started from the ultrasonic electric power output section 61 of the electric power source 26 (a step S121) simultaneously with the start of the output of the high-frequency electric power P' in the first high-frequency output mode (a step S102). At this time, in the ultrasonic output mode which is the same as the first ultrasonic output mode in the first embodiment, the vibration generating electric power P is output. Thus, an output state of the vibration generating electric power P is controlled to a state where the treatment section 17 vibrates with a fixed amplitude (a first amplitude) U1.

Moreover, like the first embodiment, steps S103 and S104 are performed, and a target peak of the ultrasonic impedance value Z is detected. when the detection processing of the target peak is carried out (the step S104), an output state of the high-frequency electric power P' is switched from the first high-frequency output mode to the second high-frequency output mode (a step S106) and, at the same time, an output of the vibration generating electric power P from the ultrasonic electric power output section 61 is stopped (a step S122). That is, on the basis of the detection of the target peak, the output of the vibration generating electric power P is stopped at the same time of or after the peak detection point. In an example shown in FIG. 16, the output of the vibration generating electric power P is stopped at a peak detection point t1+ΔT1. Additionally, the notifying section 58 notifies that the output state of the high-frequency electric power P' has been changed and the output of the vibration generating electric power P has been stopped (a step S123). Further, the output of the high-frequency electric power P' is manually or automatically stopped (a step S124).

In this modification, on the basis of the detection of the target peak, the output of the vibration generating electric power P is stopped. Thus, after the peak detection point, the treatment section 17 does not vibrate, the frictional heat due to the ultrasonic vibration is not generated. Thus, after the peak detection point, wear and thermal deformation of the pad member 43 (the abutment portion 45) in a region where the contact portion 45 comes into contact with the treatment section 17 can be further effectively reduced.

Further, even if the output of the ultrasonic electric power P is stopped, on the basis of the detection of the target peak, the output state of the high-frequency electric power P' is switched to the second high-frequency output mode where the thermal energy generated by the high-frequency current I' increases. Thus, even if the treated target H is not divided in a part of a range at the peak detection point, the treated target H is coagulated and incised at the same time in an undivided part of a range by thermal energy Q' produced due to the high-frequency current I'. That is, even if the output of the vibration generating electric power P is stopped on the basis of the detection of the target peak, it is possible to effectively prevent excessive frictional heat from being generated by the contact of the treatment section 17 and the abutment portion 45 of the jaw 18.

Figure 17:
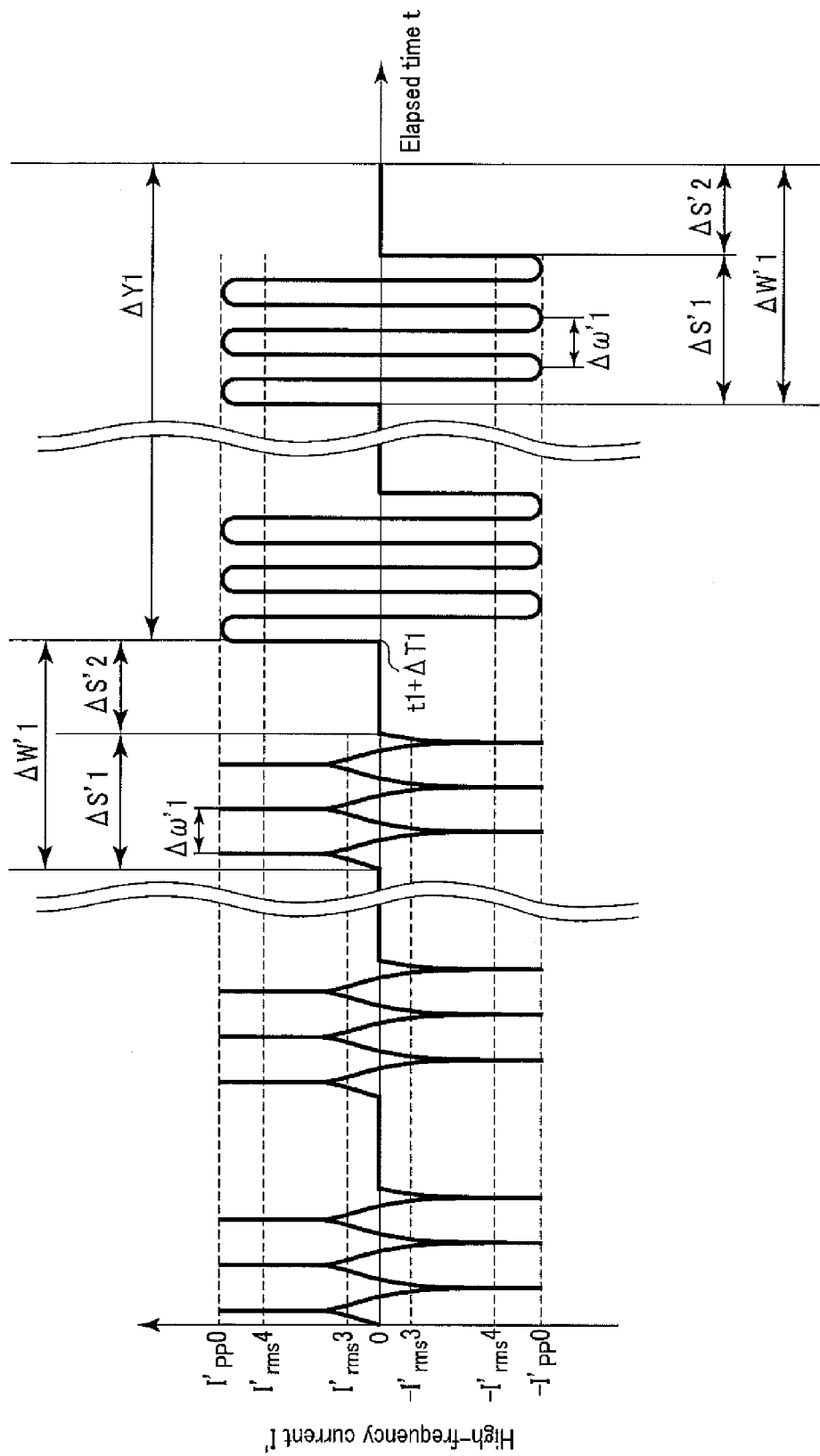
FIG. 17 is a schematic view showing an example of changes with time of the high-frequency current flowing between the treatment section and the grasping member according to a third modification.

Furthermore, in the first embodiment, the effective value I'rms of the high-frequency current I' is changed by changing the amplitude (the crest value) I'pp of the high-frequency current I' between the first high-frequency output mode and the second high-frequency output mode, it is not restricted thereto. For example, as a third modification, the first high-frequency output mode and the second high-frequency output mode may have the same amplitude I'pp of the high-frequency current I' as shown in FIG. 17. FIG. 17 shows changes with time of the high-frequency current I' in the example where the ultrasonic impedance value Z changes with time as shown in FIG. 9. In FIG. 17, an axis of ordinate represents the high-frequency current I', and an axis of abscissa represents an elapsed time t from the start of output of the high-frequency electric power P'.

As shown in FIG. 17, in this modification, the high-frequency current I' has a fixed amplitude I'pp0 in both the first high-frequency output mode and the second high-frequency output mode. However, a crest factor κ of the high-frequency current I' varies between the first high-frequency output mode and the second high-frequency output mode. The crest factor κ is as represented by Expression (4) using the amplitude (the crest value) I'pp and the effective value (the current value) I'rms.

[Expression 4]

$$\kappa = \frac{I'pp}{I'rms} \qquad (4)$$

Thus, when the amplitude I'pp of the high-frequency current I' is fixed, the effective value I'rms of the high-frequency current increases by reducing the crest factor κ.

Here, when the high-frequency current I' has a waveform of a sine wave, the crest factor κ becomes a square root of 2 (approximately 1.41). Further, when the high-frequency current I' has a waveform of a square wave (a rectangular wave), the crest factor κ becomes 1, which is a minimum value.

In this modification, the crest factor κ in the second high-frequency output mode is set to be smaller than that in the first high-frequency output mode. For example, the crest factor κ of the high-frequency current I' is 5 or more in the first high-frequency output mode, and the crest factor κ of the high-frequency current I' is a square root of 2 and the high-frequency current I' has a waveform of the sine wave in the second high-frequency output mode. As described above, when the crest factor κ is adjusted, the high-frequency current I' having a first effective value I'rms3 flows in the first high-frequency output mode, and the high-frequency current I' having a second effective value I'rms4 larger than the first effective value I'rms3 flows in the second high-frequency output mode. The crest factor κ varies when a voltage value of the high-frequency voltage V' applied between the treatment section (the probe electrode portion) 17 and the grasping member (the jaw electrode portion) 42 and an electric power value of the high-frequency electric power P' change. Thus, the high-frequency control section 69 increases the effective value I'rms of the high-frequency current I' in the second high-frequency output mode to be higher than that in the first high-frequency output mode by adjusting at least one of the voltage value of the high-frequency voltage V' and the electric power value of the high-frequency electric power P'.

In this modification, likewise, the effective value I'rms of the high-frequency current I' in the second high-frequency output mode is higher than that in the first high-frequency output mode. Thus, in the second high-frequency output mode, the thermal energy Q' generated by the high-frequency current I' increases. When the thermal energy Q' increases, the incision performance provided by the high-frequency current I' in the second high-frequency output mode is higher than that in the first high-frequency output mode.

It is to be noted that, in a given modification, both the amplitude I'pp of the high-frequency current I' and the crest factor κ may be changed between the first high-frequency output mode and the second high-frequency output mode. In this case, the effective value I'rms of the high-frequency current I' in the second high-frequency output mode is increased to be higher than that in the first high-frequency output mode by changing both the amplitude I'pp of the high-frequency current I' and the crest factor κ.

Figure 18:
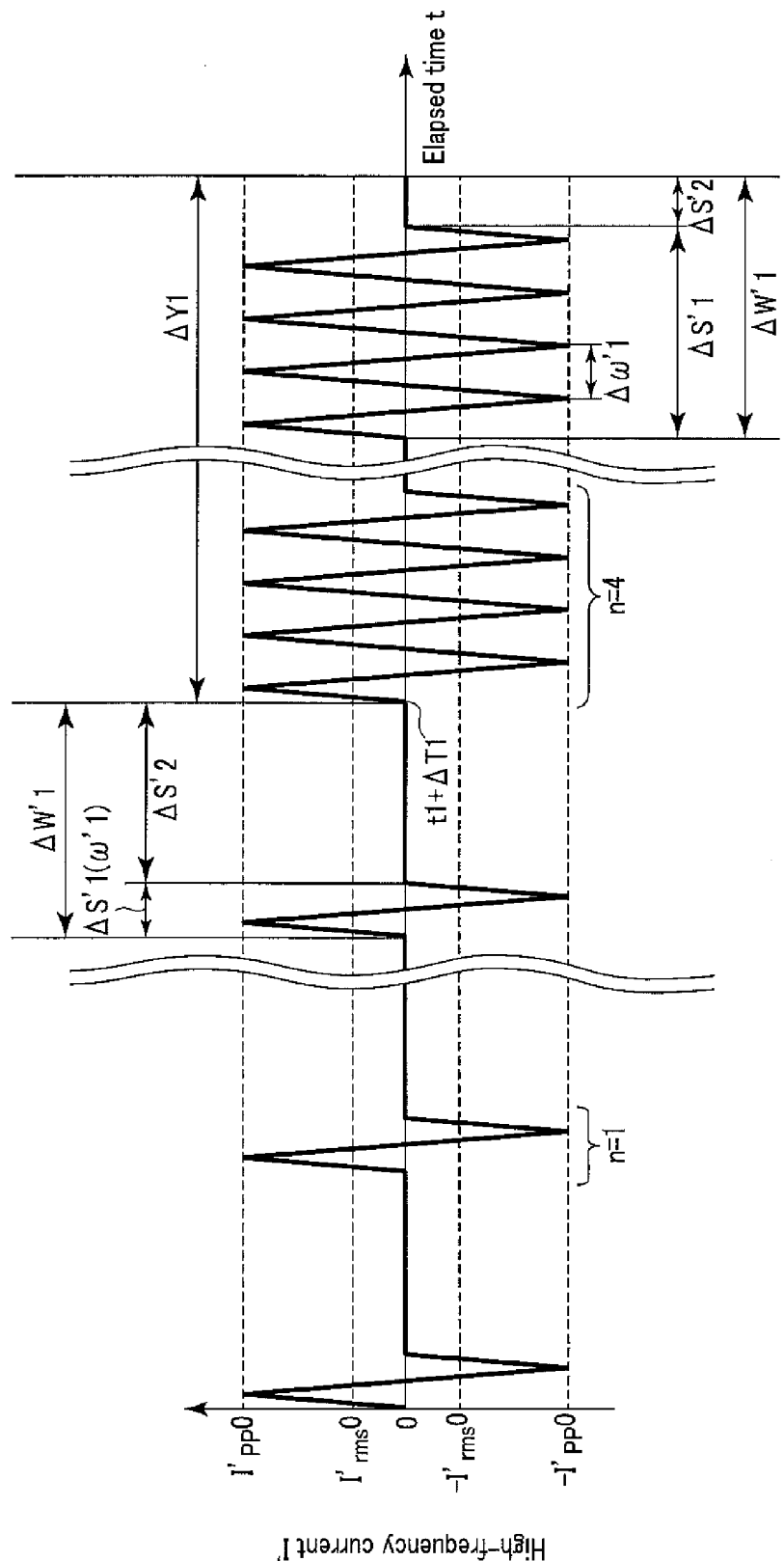
FIG. 18 is a schematic view showing an example of changes with time of the high-frequency current flowing between the treatment section and the grasping member according to a fourth modification.

Moreover, as a fourth modification, the first high-frequency output mode and the second high-frequency output mode may have the same effective value I'rms of the high-frequency current I' as shown in FIG. 18. FIG. 18 shows changes with time of the high-frequency current I' in the example where the ultrasonic impedance value Z changes with time as shown in FIG. 9. In FIG. 18, an axis of ordinate represents the high-frequency current I', and an axis of abscissa represents an elapsed time t from the start of output of the high-frequency electric power P'.

As shown in FIG. 18, in this modification, the high-frequency current I' has a fixed amplitude (a crest value) I'pp0 and a fixed effective value I'rms0 in both the first high-frequency output mode and the second high-frequency output mode. Further, in the first high-frequency output mode and the second high-frequency output mode, an output state of the high-frequency electric power P' is periodically modulated (changed) in a modulation cycle (a high-frequency modulation cycle) ΔW'. In an example shown in FIG. 18, the output state of the high-frequency electric power P' is modulated in a modulation cycle ΔW'1 in each of the first high-frequency output mode and the second high-frequency output mode. However, in this modification, a ratio γ' of the output stage ΔS'1 (a duty ratio of the output stage ΔS'1) during the modulation cycle ΔW' (ΔW'1) in the second high-frequency output mode is larger than that in the first high-frequency output mode. That is, in the second high-frequency output mode, the output stage ΔS'1 where the high-frequency electric power P' is output is longer and the non-output stage ΔS'2 where the high-frequency electric power P' is not output is shorter than those in the first high-frequency output mode. When a time of the output stage ΔS'1 is long, a wave number n of the high-frequency current I' in one output stage ΔS'1 in the second high-frequency output mode is higher than that in the first high-frequency output mode. For example, the wave number n of the high-frequency current I' in the one output stage ΔS'1 in the first high-frequency output mode is 1, and the wave number n of the high-frequency current I' in the one output stage ΔS'1 in the second high-frequency output mode is 4.

When the high-frequency electric power P' is intermittently output, the thermal energy Q' generated by the high-frequency current I' is affected by the ratio γ' of the output stage ΔS'1 during the modulation cycle ΔW' in addition to the effective value I'rms of the high-frequency current I'. That is, since the duty ratio γ' of the output stage ΔS'1 is raised, the thermal energy Q' is increased. In this modification, the duty ratio γ' of the output stage ΔS'1 in the second high-frequency output mode is higher than that in the first high-frequency output mode. Thus, in the second high-frequency output mode, the thermal energy Q' generated by the high-frequency current I' becomes large. When the thermal energy Q' becomes large, the incision performance provided by the high-frequency current I' in the second high-frequency output mode is higher than that in the first high-frequency output mode.

Figure 19:
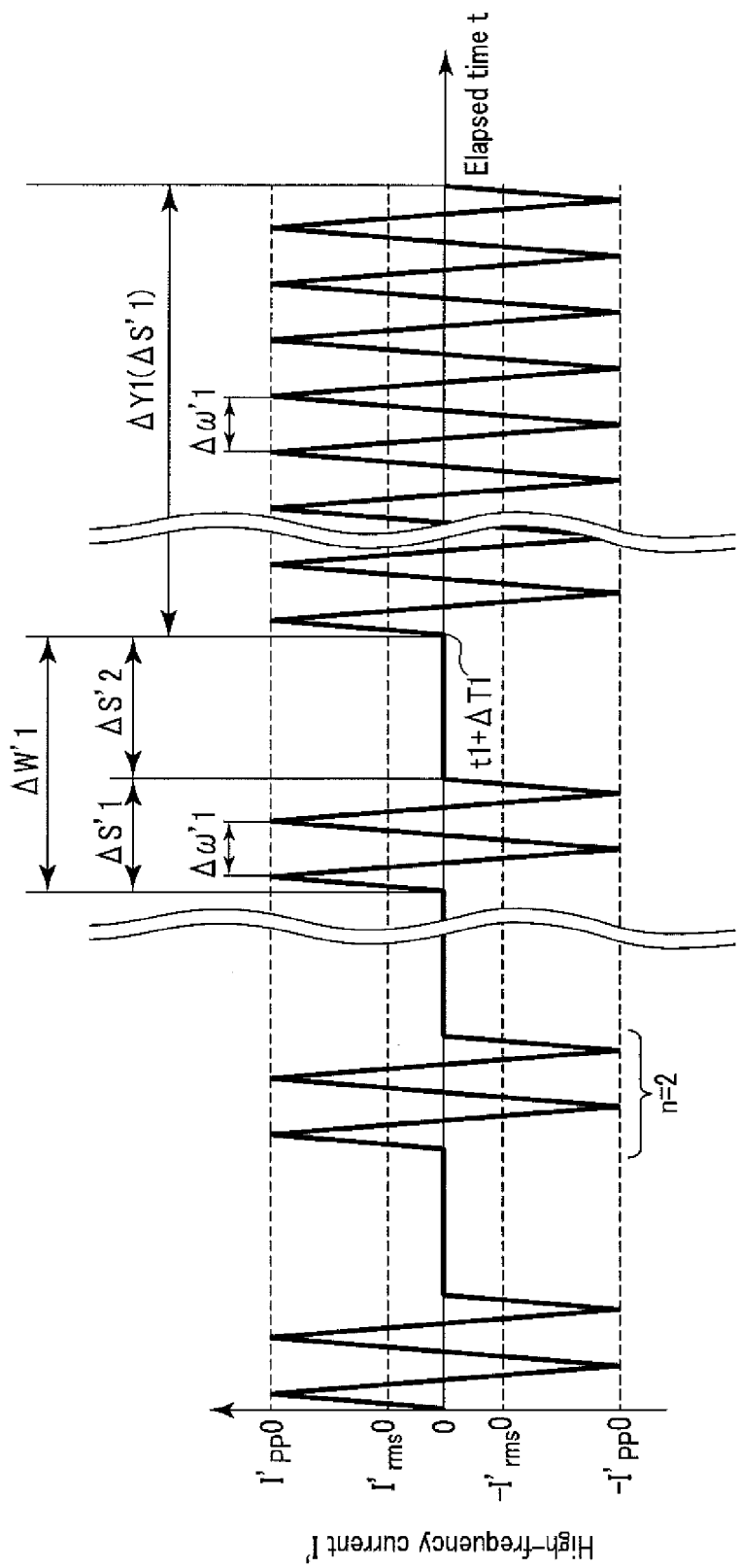
FIG. 19 is a schematic view showing an example of changes with time of the high-frequency current flowing between the treatment section and the grasping member according to a fifth modification.

Furthermore, as a fifth modification, in the second high-frequency output mode, the high-frequency power P' may not be intermittently output as shown in FIG. 19. FIG. 19 shows changes with time of the high-frequency current I' in the example where the ultrasonic impedance value Z changes with time as shown in FIG. 9. In FIG. 19, an axis of ordinate represents the high-frequency current I', and an axis of abscissa represents an elapsed time t from the start of output of the high-frequency electric power P'.

In this modification, like the first embodiment, the high-frequency electric power P' is intermittently output in the first high-frequency output mode. In the first high-frequency output mode, the wave number n in one output stage ΔS'1 is 2. However, in this modification, an output state of the high-frequency electric power P' from the high-frequency electric power output section 62 is controlled so that continuous output of continuously outputting the high-frequency electric power P' is performed with time in the second high-frequency output mode. That is, in the second high-frequency output mode, the output stage ΔS'1 is continuously maintained with time. Thus, in the second high-frequency output mode, the duty ratio γ' of the output stage ΔS'1 is 100%.

When the high-frequency electric power P' is continuously output, the duty ratio γ' of the output stage ΔS'1 becomes 100%, and the duty ratio γ' of the output stage ΔS'1 is higher than that in a case where the intermittent output is performed. Thus, the thermal energy Q' in the second high-frequency output mode where the high-frequency electric power P' is continuously output is larger than that in the first high-frequency output mode where the high-frequency power P' is intermittently output. When the thermal energy Q' becomes large, the incision performance provided by the high-frequency current I' in the second high-frequency output mode is higher than that in the first high-frequency output mode.

Moreover, as a sixth modification, in both the first high-frequency output mode and the second high-frequency output mode, the high-frequency electric power P' may be continuously output as shown in FIG. 20. FIG. 20 shows changes with time of the high-frequency current I' in the example where the ultrasonic impedance value Z changes with time as shown in FIG. 9. In FIG. 20, an axis of ordinate represents a high-frequency current I', and an axis of abscissa represents an elapsed time t from the start of output of the high-frequency electric power P.

As shown in FIG. 20, in this modification, the continuous output is performed in both the first high-frequency output mode and the second high-frequency output mode. Additionally, the effective value I'rms of the high-frequency current I' in the second high-frequency output mode is raised to be higher than that in the first high-frequency output mode. The high-frequency current I' has a first effective value I'rms5 in the first high-frequency output mode, and the high-frequency current I' has a second effective value I'rms6 higher than the first effective value I'rms5 in the second high-frequency output mode. As described above, in the second high-frequency output mode, the effective value I'rms of the high-frequency current I' can be raised to be higher than that in the first high-frequency output mode by adjusting the amplitude I'pp of the high-frequency current I' and the crest factor κ. In this modification, the high-frequency current I' has a first amplitude I'pp5 in the first high-frequency output mode, and the high-frequency current I' has a second amplitude I'pp6 higher than the first amplitude I'pp5 in the second high-frequency output mode.

In this modification, likewise, the effective value I'rms of the high-frequency current I' in the second high-frequency output mode is higher than that in the first high-frequency output mode. Thus, in the second high-frequency output mode, the thermal energy Q' generated by the high-frequency current I' becomes large. When the thermal energy Q' becomes large, the incision performance provided by the high-frequency current I' in the second high-frequency output mode is higher than that in the first high-frequency output mode.

It is to be noted that elements in the foregoing embodiment and modifications may be changed between the first high-frequency output mode and the second high-frequency output mode. For example, in a given modification, when the first high-frequency output mode is switched to the second high-frequency output mode, the intermitted output is switched to the continuous output, and the effective value I'rms of the high-frequency current I' in the second high-frequency output mode becomes higher than that in the first high-frequency output mode.

Further, in a given modification, after the start of output of the ultrasonic electric power P, a frequency f of the ultrasonic vibration may be adjusted by PLL (Phase Locked Loop) control. In this case, after the start of adjustment at which the adjustment of the frequency f of the ultrasonic vibration starts, detection processing of a minimal value of the ultrasonic impedance value Z is carried out. Here, assuming that a time point at which a minimal value Z is first detected after the start of adjusting of the frequency f is a minimal detection point, a detection disallowed state where a detection of a target peak is not executed is switched to a detection allowed state where the detection of the target peak is performed by the control section 51 at the minimal detection point. That is, the peak detecting section 53 is controlled so that the detection of the target peak is not executed until the minimal detection point.

Furthermore, in another modification in which the frequency f is adjusted by the PLL control, at the time of startup which is a time point reached after elapse of a predetermined set time from the adjustment start point of the frequency f, the control section 51 may switch the detection disallowed state where the detection of the target peak is not performed to the detection allowed state where the detection of the target peak is executed. That is, in this modification, the peak detecting section 53 is controlled so that the detection of the target peak is not executed until the startup.

Moreover, in a given modification, a switching operating section which is configured to input a switching operation between the detection disallowed state (a non-detection state) where the peak detecting section 53 does not execute the detection and judgement (determination) of the target peak and the detection allowed state where the peak detecting section 53 execute the detection of the target peak may be provided in the control unit 3 or the like.

Additionally, in the comparison of changes with time of the ultrasonic impedance value Z to the held tentative peak value (the step S113 in FIG. 13) and the judgment on the target peak (the step S114), the high-frequency impedance value Z' of the high-frequency electric power P' may be used. For example, in a given modification, a length of a reference time ΔT and magnitude of a reference decrement ϵ adopted for the comparison are determined on the basis of the high-frequency impedance value Z.

In the foregoing embodiment and modifications, the grasping treatment apparatus (1) includes the impedance detecting section (52) configured to detect the ultrasonic impedance value (Z) of the vibration generating electric power (P) with time in a state where the vibration generating electric power (P) is output from the electric power source (26), and the gradual decrease detecting section (55) configured to detect the gradual decrease start point at which the ultrasonic impedance value (Z) starts to gradually decrease on the basis of a detection result in the impedance detecting section (52). Furthermore, the grasping treatment apparatus (1) includes the tentative peak value holding section (56) configured to hold the ultrasonic impedance value (Z) at the detected gradual decrease start point as a tentative peak value, and the peak judging section (57) configured to judge whether the held tentative peak value is a target peak which is a detection target by comparing changes with time of the ultrasonic impedance value (Z) after the gradual decrease start point to the held tentative peak value. Moreover, the grasping treatment apparatus (1) includes the ultrasonic control section (59) configured to stop the output of the vibration generating electric power (P) from the electric power source (26) or configured to enable the electric power source (26) to output the vibration generating electric power (P) in the second ultrasonic output mode where the incision performance provided by the ultrasonic vibration in the treatment section (17) is smaller than that in the first ultrasonic output mode before the peak detection point at which the target peak is detected on the basis of the detection of the target peak. Additionally, the grasping treatment apparatus (1) includes the high-frequency control section (69) configured to enable the electric power source (26) to output the high-frequency electric power (P') in the second high-frequency output mode where the incision performance provided by the high-frequency current (I') flowing between the probe electrode portion (17) and the jaw electrode portion (42) becomes larger than that in the first high-frequency output mode before the peak detection point, on the basis of the detection of the target peak.

Hereinafter, characteristic matters will be added.

Remarks (Added Matter 1)

In a grasping treatment apparatus including a vibration generating section configured to generate an ultrasonic vibration when a vibration generating electric power is supplied, a treatment section to which the ultrasonic vibration generated in the vibration generating section and high-frequency electric power are transmitted, which is configured to perform a treatment by use of the transmitted ultrasonic vibration and high-frequency electric power, and which includes a probe electrode portion configured to function as an electrode when the high-frequency electric power is supplies thereto, and a jaw which is openable and closable relative to the treatment section, and which includes an abutment portion abatable with the treatment section in a state where the jaw is closed relative to the treatment section, and a jaw electrode portion configured to function as an electrode different from the probe electrode portion when the high-frequency electric power is transmitted thereto, a control unit configured to control a supply of vibration generating electric power to the vibration generating section and a supply of the high-frequency electric power to the probe electrode portion and the jaw electrode portion, the control unit comprising:

an electric power source configured to output the vibration generating electric power and the high-frequency electric power, an impedance detecting section configured to detect an ultrasonic impedance value of the vibration generating electric power with time, in a state where the vibration generating electric power is output from the electric power source, a gradual decrease detecting section configured to detect a gradual decrease start point to start gradual decrease of the ultrasonic impedance value on the basis of detection result in the impedance detecting section, a tentative peak value holding section configured to hold the ultrasonic impedance value at the detected gradual decrease start point as a tentative peak value, a peak judging section configured to judge whether or not the held tentative peak value is a target peak of a detection target by comparing, to the held tentative peak value, changes with time of the ultrasonic impedance value after the gradual decrease start point, an ultrasonic control section configured to control an output state of the vibration generating electric power from the electric power source, the ultrasonic control section being configured to stop output of the vibration generating electric power from the electric power source, or to output the vibration generating electric power from the electric power source in a second ultrasonic output mode where incision performance provided by the ultrasonic vibration in the treatment section becomes smaller than that in a first ultrasonic output mode before a judgment point at which the tentative peak value is determined to be the target peak, on the basis of the fact that the tentative peak value is determined to be the target peak value by the peak judging section, and a high-frequency control section configured to control an output state of the high-frequency electric power from the electric power source, the high-frequency control section being configured to output the high-frequency electric power from the electric power source in a second high-frequency output mode where incision performance provided by a high-frequency current flowing between the probe electrode portion and the jaw electrode portion becomes higher than that in a first high-frequency output mode before the judgment point, on the basis of the fact that the tentative peak value is determined to be the target peak by the peak judging section.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A grasping treatment apparatus comprising:
an electric power source configured to output a vibration generating electric power and a high-frequency electric power;
an ultrasonic transducer configured to generate an ultrasonic vibration by the vibration generating electric power from the electric power source;
a treatment section that includes a probe electrode portion configured to function as an electrode when the high-frequency electric power is supplied, thereto, and which is configured to perform a treatment by use of the ultrasonic vibration generated in the ultrasonic transducer and the high-frequency electric power from the electric power source;
a jaw which is openable and closable relative to the treatment section;
a jaw electrode portion which is provided to the jaw, and which is configured to function as an electrode different from the probe electrode portion when the high-frequency electric power is supplied thereto;
an impedance detecting section configured to detect an ultrasonic impedance value related to the vibration generating electric power;
a peak judging section configured to detect a peak of the ultrasonic impedance value based on the ultrasonic impedance value detected by the impedance detecting section;
an ultrasonic control section that is configured to stop an output of the vibration generating electric power from the electric power source or configured to switch an output state of the vibration generating electric power from the electric power source from a first ultrasonic output mode to a second ultrasonic output mode when the peak is detected by the peak judging section, an average of a vibration velocity in the treatment section during a predetermined unit time being lower in the second ultrasonic output mode than that in the first ultrasonic output mode; and
a high-frequency control section which is configured to switch an output state of the high-frequency electric power from the electric power source from a first high-frequency output mode to a second high-frequency output mode when the peak is detected by the peak judging section, thermal energy generated by a high-frequency current flowing between the probe electrode portion and the jaw electrode portion being higher in the second high-frequency output mode than that in the first high-frequency output mode.

2. The grasping treatment apparatus according to claim 1, wherein, in the second high-frequency output mode, the high-frequency control section is configured to increase an effective value of the high-frequency current to be larger than that in the first high-frequency output mode.

3. The grasping treatment apparatus according to claim 2, wherein, in the second high-frequency output mode, the high-frequency control section is configured to increase the effective value of the high-frequency current to be larger than that in the first high-frequency output mode by performing at least one of an increase in an amplitude of the high-frequency current to be larger than that in the first high-frequency output mode and a decrease in a crest factor of the high-frequency current to be smaller than that in the first high-frequency output mode.

4. The grasping treatment apparatus according to claim 2, wherein, in the second high-frequency output mode, the high-frequency control section is configured to increase the effective value of the high-frequency current to be larger than that in the first high-frequency output mode by adjusting at least one of a voltage value of a high-frequency voltage applied between the probe electrode portion and the jaw electrode portion in a state where the high-frequency electric power is output and an electric power value of the high-frequency electric power.

5. The grasping treatment apparatus according to claim claim 1,
wherein the high-frequency control section is configured to control the output state of the high-frequency electric power from the electric power source so that the high-frequency electric power is intermittently output in the first high-frequency output mode and the high-frequency electric power is continuously output in the second high-frequency output mode.

6. The grasping treatment apparatus according to claim 1, wherein the high-frequency control section is configured to control the output state of the high-frequency electric power from the electric power source so that the high-frequency electric power is intermittently output in each of the first high-frequency output mode and the second high-frequency output mode,
the high-frequency control section is configured to periodically change the output state of the high-frequency power in a modulation cycle between an output stage where the high-frequency electric power is output and a non-output stage where the high-frequency electric power is not output in each of the first high-frequency output mode and the second high-frequency output mode, and
the high-frequency control section is configured to increase a ratio of the output stage during the modulation cycle in the second high-frequency output mode to be higher than that in the first high-frequency output mode.

7. The grasping treatment apparatus according to claim 6, wherein, in the second high-frequency output mode, the high-frequency control section is configured to increase a wave number of the high-frequency current in one output stage to be larger than that in the first high-frequency output mode by increasing a time of the one output stage to be longer than that in the first high-frequency output mode.

8. The grasping treatment apparatus according to claim 1, wherein the impedance detecting section is configured to detect a vibration generating current and a vibration generating voltage, and configured to detect the ultrasonic impedance value based on the detected vibration generating current and vibration generating voltage.

9. The grasping treatment apparatus according to claim 1, further comprising a notifying section configured to notify that the output state of the high-frequency electric power from the electric power source has been switched after switching the first high-frequency output mode to the second high-frequency output mode.

10. The grasping treatment apparatus according to claim 1, further comprising:
a gradual decrease detecting section configured to detect a gradual decrease start point to start gradual decrease of the ultrasonic impedance value based on the ultrasonic impedance value detected by the impedance detecting section; and
a tentative peak value holding section configured to hold the ultrasonic impedance value at the detected gradual decrease start point as a tentative peak value;
wherein the peak judging section is configured to compare a variation with time of the ultrasonic impedance value after the gradual decrease start point relative to the tentative peak value held by the tentative peak value holding section, thereby judging whether or not the held tentative peak value is the peak.

11. The grasping treatment apparatus according to claim 1,
wherein the ultrasonic control section is configured to control the output state of the vibration generating electric power from the electric power source so that an amplitude in the treatment section is smaller in the second ultrasonic output mode than that in the first ultrasonic output mode.

* * * * *